(12) United States Patent
Wang et al.

(10) Patent No.: US 8,834,776 B2
(45) Date of Patent: Sep. 16, 2014

(54) CONTROL OF DEGRADATION PROFILE OF BIOABSORBABLE POLY(L-LACTIDE) SCAFFOLD

(75) Inventors: Yunbing Wang, Sunnyvale, CA (US); Xiao Ma, Santa Clara, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 576 days.

(21) Appl. No.: 13/104,732

(22) Filed: May 10, 2011

(65) Prior Publication Data
US 2012/0290070 A1     Nov. 15, 2012

(51) Int. Cl.
*A61F 2/82* (2013.01)

(52) U.S. Cl.
USPC .......................... 264/485; 264/488; 623/1.38

(58) Field of Classification Search
USPC .................................. 264/488, 485; 623/1.38
See application file for complete search history.

(56) References Cited

U.S. PATENT DOCUMENTS

| | | | |
|---|---|---|---|
| 6,716,957 B2 | 4/2004 | Tunc | |
| 7,524,891 B2 | 4/2009 | Rose et al. | |
| 7,794,776 B1 | 9/2010 | Limon et al. | |
| 2003/0069629 A1 | 4/2003 | Jadhav et al. | |
| 2007/0179276 A1 | 8/2007 | Krul et al. | |
| 2007/0203564 A1* | 8/2007 | Rusk et al. | 623/1.13 |
| 2007/0253999 A1 | 11/2007 | Huang et al. | |
| 2009/0246253 A1* | 10/2009 | Ding | 424/426 |
| 2009/0324670 A1* | 12/2009 | Wang | 424/423 |
| 2011/0022155 A1 | 1/2011 | Wang et al. | |
| 2012/0091633 A1 | 4/2012 | Wang et al. | |

FOREIGN PATENT DOCUMENTS

| | | |
|---|---|---|
| EP | 1 184 008 | 3/2002 |
| WO | WO 2007/106158 | 9/2007 |
| WO | WO 2007/146354 | 12/2007 |
| WO | WO 2011/011242 | 1/2011 |
| WO | WO 2011/123194 | 10/2011 |
| WO | WO 2011/123209 | 10/2011 |
| WO | WO 2012/051195 | 4/2012 |
| WO | WO 2012/148452 | 11/2012 |

OTHER PUBLICATIONS

Bergsma et al., Biocompatibility and degradation mechanisms of predegraded and non-predegraded poly(lactide) implants: an animal study, J. of Materials Science: Materials in Medicine, vol. 6 (1995), pp. 715-724.*
Bergsma et al., In vitro predegradation at elevated temperatures of poly(lactide), J. of Materials Science: Materials in Medicine, vol. 6 (1995), pp. 642-646.*
Loo et al., Degradation of poly(lactide-co-glycolide) (PLGA) and poly(l-lactide) (PLLA) by electron beam radiation, Biomaterials, vol. 26, No. 12 (2005), pp. 1359-1367.*
Loo et al., Hydrolytic degradation of electron beam irradiated high molecular weight and non-irradiated moderate molecular weight PLLA, Acta Biomaterialia, vol. 2, No. 3 (2006), pp. 287-296.*

(Continued)

*Primary Examiner* — Matthew Daniels
(74) *Attorney, Agent, or Firm* — Squire Patton Boggs (US) LLP

(57) ABSTRACT

Methods of controlling the degradation profile of a biodegradable stent scaffolding are disclosed. Disclosed methods include controlling features of the degradation profile including the time to loss of radial strength and the degradation time of the stent.

3 Claims, 13 Drawing Sheets

(56) References Cited

OTHER PUBLICATIONS

Plikk et al., Finalizing the properties of porous scaffolds of aliphatic polyesters through radiation sterilization, Biomaterials, vol. 27, No. 31 (2006), pp. 5335-5347.*
De Jong et al., Tissue response to partially in vitro predegraded poly-L-lactide implants, Biomaterials, vol. 26, No. 14 (2005), pp. 1781-1791.*
International Search Report for PCT/US2011/025074, mailed May 31, 2011, 14 pgs.
International Search Report for PCT/US2010/041998, mailed Feb. 10, 2011, 6 pgs.
Bendix "Chemical synthesis of polylactide and its copolymers for medical applications", Pol. Degrad. and Stability 59, pp. 129-135 (1998).
Di Mario et al., "Quantitative assessment with intracoronary ultrasound of the mechanisms of restenosis after percutaneous transluminal coronary angioplasty and directional coronary atherectomy", Am J Cardiol, 75 (12), pp. 772-777 (1995).
Hayashi "Biodegradable polymers for biomedical uses", Progress in Polymer Science 19 (4) pp. 663-702 (1994).
Serruys et al., "Incidence of restenosis after successful coronary angioplasty: a time-related phenomenon. A quantitative angiographic study in 342 consecutive patients at 1, 2, 3, and 4 months", Circulation 77, pp. 361-371 (1988).
Hyon et al., "Effects of residual monomer on the degradation of DL-lactide polymer", Polymer Int. vol. 46, No. 3, pp. 196-202, Abstract 1 pg. (1998).
Kimura et al., "Remodeling of human coronary arteries undergoing coronary angioplasty or atherectomy", Circulation 96 (2), pp. 475-483 (1997).
Luo et al., "Coronary artery restenosis after balloon angioplasty in humans is associated with circumferential coronary constriction", Arterioscler. Thromb. Vasc. Biol. 16 (11), pp. 1393-1398 (1996).
Mintz et al., "Arterial remodeling after coronary angioplasty: a serial intravascular ultrasound study", Circulation 94 (1), pp. 35-43 (1996).
Nakamura et al., "Bioabsorption of polylactides with different molecular properties", J. of Biomed. Mat. Res. vol. 23 pp. 1115-1129 (1989).
Nobuyoshi et al., "Restenosis after successful percutaneous transluminal coronary angioplasty: serial angiographic follow-up of 229 patients", J. Am. Coll. Cardiol. 12 (3), pp. 616-623 (1988).
Ormiston et al., "Bioabsorbable Coronary Stents", Circ. Cardiovasc. Intervent. 2, pp. 255-260 (2009).
Pistner et al., "Poly(L-lactide): a long-term degradation study in vivo. Part III. Analytical characterization", Biomaterials 14 (4), pp. 291-298 (1993).
Pitt et al., "Aliphatic polyesters. I. The degradation of Poly($\epsilon$-caprolactone) in Vivo", J. of Applied Pol. Science 26, pp. 3779-3787 (1981).
Pitt et al., "Aliphatic polyesters. II. The degradation of poly (DL-lactide), poly($\epsilon$-caprolactone), and their copolymers in vivo", Biomaterials 2, pp. 215-220 (1981).
Tammela et al., "Biodegradable urethral stents", BJU International 92, pp. 843-850 (2003).
Weir et al., "Degradation of poly-L-Lactide. Part I: In vitro and in vivo physiological temperature degradation", J. of Engineering in Medicine 218, pp. 307-319 (2004).
Weir et al., "Degradation of poly-L-lactide. Part 2: Increased temperature accelerated degradation", J. of Eng. In Medicine 218, pp. 321-330 (2004).
International Search Report and Written Opinion for PCT/US2012/037104, mailed Feb. 27, 2013, 14 pgs.

* cited by examiner

CONTROL OF DEGRADATION PROFILE OF BIOABSORBABLE POLY(L-LACTIDE) SCAFFOLD

BACKGROUND OF THE INVENTION

1. Field of the Invention

This invention relates to methods of treatment of blood vessels with bioabsorbable polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be have sufficient radial strength so that it is capable of withstanding the structural loads, namely radial compressive forces imposed on the stent as it supports the walls of a vessel. "Radial strength" of a stent is defined as the pressure at which a stent experiences irrecoverable deformation. The loss of radial strength is followed by a gradual decline of mechanical integrity Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Coronary artery disease treatment has experienced three revolutions since 1970s. The first one is balloon angioplasty in the 1970s, followed by metallic stent in 1990s, and the third one is metallic drug eluting stent (DES) in 2000s. Currently, all market available metallic DESs are made from biostable metals, which stay in the body permanently after implantation, make any further non-invasive screening or re-intervention more difficult.

Stents made from biostable or non-erodible materials, such as metals, have become the standard of care for percutaneous coronary intervention (PCI) as well as in peripheral applications, such as the superficial femoral artery (SFA), since such stents have been shown to be capable of preventing early and later recoil and restenosis.

In order to effect healing of a diseased blood vessel, the presence of the stent is necessary only for a limited period of time. The development of a bioresorbable stent or scaffold could obviate the permanent metal implant in vessel, allow late expansive luminal and vessel remodeling, and leave only healed native vessel tissue after the full absorption of the scaffold. Stents fabricated from biodegradable, bioabsorbable, and/or bioerodable materials such as bioabsorbable polymers can be designed to completely erode only after or some time after the clinical need for them has ended. Consequently, a fully bioabsorbable stent can reduce or eliminate the risk of potential long-term complications and of late thrombosis, facilitate non-invasive diagnostic MRI/CT imaging, allow restoration of normal vasomotion, provide the potential for plaque regression. In addition, the bioabsorbable stents do not permanently jail side branches or curtail the future use of noninvasive imaging for follow-up.

Unlike a durable stent, the properties of a bioabsorbable stent change dramatically with time once implanted. The ability of the stent to provide adequate treatment depend not only its initial properties, but also its properties as a function time, or its degradation profile. The degradation profile will influence behaviors essential to adequate treatment such as the time period that the stent can support a lumen at a deployed diameter and the time for complete bioabsorption.

In summary, fully bioresorbable scaffolds have the potential to restore vascular integrity as a brand new vascular restoration therapy, which is expected to be the fourth revolution of vascular disease treatment. Although this new concept is very exciting, so far most bioresorbable scaffold projects developed by various companies and institutes are far away from real commercialization. One important reason is that for a lot of researchers in this area, although they may have focused work for scaffold quality control at time zero (i.e., at the time of implantation before degradation begins in the lumen), they have not adequately addressed ways for degradation profile control.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a method of making a bioabsorbable stent comprising: providing a bioabsorbable polymer; selecting a desired degradation time range for a bioabsorbable implanted stent scaffolding to completely absorb after implantation; determining a range of Mn(0) for the stent made from the bioabsorbable polymer that provides the degradation time range for a finished stent, wherein the determined range of Mn(0) of the finished stent is determined from a degradation kinetic model of the bioabsorbable polymer, and making a stent scaffolding from the bioabsorbable polymer, wherein the stent scaffolding has an Mn(0) within the determined range of Mn(0).

Further embodiments of the present invention include a method of making a bioabsorbable stent comprising: providing a bioabsorbable polymer; selecting a desired minimum patency time for a bioabsorbable implanted stent scaffolding to provide at an implant site; determining an Mn at loss of radial strength of the bioabsorbable stent scaffolding made from the bioabsorbable polymer; determining Mn(0) of the stent scaffolding made from the bioabsorbable polymer that provides an Mn at the desired minimum patency time equal to the Mn at loss of radial strength, wherein the determined Mn(0) is determined from a degradation kinetic model of the bioabsorbable polymer, and making a stent scaffolding from the bioabsorbable polymer, wherein the stent scaffolding has an Mn(0) greater than or equal to the determined Mn(0).

Additional embodiments of the present invention include a method of making a bioabsorbable stent comprising: providing a bioabsorbable polymer, wherein the bioabsorbable polymer is made of repeat units formed through polymerization reaction of a monomer; selecting a desired degradation time range for a bioabsorbable implanted stent scaffolding to completely absorb after implantation; determining a range of the monomer content in the bioabsorbable polymer to provide the degradation time range for a stent scaffolding, wherein the determined range of monomer content is determined from a degradation kinetic model of the bioabsorbable polymer, and making a stent scaffolding from the bioabsorbable polymer, wherein the stent scaffolding has a monomer content within the determined range.

Other embodiments of the present invention include a method of making a bioabsorbable stent comprising: providing a bioabsorbable polymer, wherein the bioabsorbable polymer is made of repeat units formed through polymerization reaction of a monomer; selecting a desired minimum patency time for a bioabsorbable implanted stent scaffolding; determining an Mn at loss of radial strength of the bioabsorbable stent scaffolding made from the bioabsorbable polymer; determining a monomer content in the bioabsorbable polymer of the finished stent that provides an Mn at the desired minimum patency time that is equal to the Mn at loss of radial strength, wherein the determined monomer content is determined from a degradation versus monomer content model of the bioabsorbable polymer, and making a stent scaffolding from the bioabsorbable polymer, wherein the bioabsorbable polymer of stent scaffolding has a monomer content less than or equal to the determined monomer content.

Additional embodiments of the present invention include a method of making a bioabsorbable stent comprising: providing a bioabsorbable polymer scaffolding made from PLLA prior to a radiation exposure step, wherein the Mn of the PLLA of the scaffolding is at least about 250 kDa; selecting a desired minimum patency time for a PLLA scaffolding to provide at an implant site; providing an Mn at loss of radial strength during degradation of a PLLA scaffolding; determining an Mn(0) of a PLLA scaffolding that provides an Mn of the PLLA scaffolding at the desired minimum patency time equal to the Mn at loss of radial strength; and performing a sterilization step comprising exposing the PLLA scaffolding to a radiation dose between 31 to 75 kGy which reduces the Mn of the PLLA scaffolding to no less than the Mn(0).

Other embodiments of the present invention include a method of making a bioabsorbable stent comprising: providing a PLLA polymer scaffolding, wherein the PLLA polymer tube has an Mn of at least 250 kDa; exposing the laser cut scaffolding to a first radiation dose prior to crimping to reduce the Mn; crimping the exposed scaffolding to a reduced diameter over a delivery balloon; and exposing the crimped scaffolding to a second radiation dose of 20-31 kGy for sterilization which reduces the Mn to an Mn(0), wherein the Mn(0) provides a degradation time of 16-20 months and a time of loss of radial strength of at least about 3 months.

Certain embodiments of the present invention include a method of making a bioabsorbable stent comprising: providing a bioabsorbable polymer scaffolding made from PLLA prior to a radiation exposure step, wherein the Mn of the PLLA of the scaffolding is at least about 250 kDa; and exposing the scaffolding to radiation for sterilization, wherein the radiation reduces the Mn of the scaffolding to 70 kDa or less, wherein the Mn of the exposed scaffolding provides a degradation time of the exposed scaffold of less than 18 months and the time to loss of radial strength is at least 3 months.

Additional embodiments of the present invention include a method of fabricating a stent comprising: providing PLLA resin having an Mn between 150 to 200 kD; processing the PLLA to form a PLLA scaffolding; forming a coating on the PLLA scaffolding comprising PDLLA with an Mn between 80-100 kDa; exposing the coated scaffold to radiation for sterilization, wherein the radiation exposure reduces the Mn of the PLLA scaffolding to 70 kDa or lower.

Other embodiments of the present invention include a method of fabricating a stent comprising: providing a bioabsorbable polymer resin; extruding the polymer resin to form a tube; radially expanding the polymer tube; fabricating a stent scaffolding from the expanded tube; and radiation sterilizing the scaffolding; and hydrolytically pre-degrading at least one of the following to reduce its Mn: resin, the extruded tube; or the radially expanded tube.

Additional embodiments of the present invention include a method of fabricating a stent comprising: fabricating a PLLA stent scaffolding made of a biodegradable stent scaffolding, wherein the Mn of the PLLA stent scaffolding is greater than 250 kDa; hydrolytically pre-degrading the PLLA stent scaffolding prior to radiation sterilization to reduce the Mn of the scaffolding to 100 kDa or less, wherein the pre-degradation provides a degradation time of the scaffolding of less than 18 months.

DETAILED DESCRIPTION OF THE INVENTION

Coronary arteries refer generally to arteries that branch off the aorta to supply the heart muscle with oxygenated blood. Peripheral arteries refer generally to blood vessels outside the heart and brain. In both coronary artery disease and peripheral artery disease, the arteries become hardened and narrowed or stenotic and restrict blood flow. In the case of the coronary arteries, blood flow is restricted to the heart, while in the peripheral arteries blood flow is restricted leading to the kidneys, stomach, arms, legs, and feet. The narrowing is caused by the buildup of cholesterol and other material, called plaque, on the inner walls of the vessel. Such narrowed or stenotic portions are often referred to as lesions. Artery disease also includes the reoccurrence of stenosis or restenosis that occurs after an angioplasty treatment. Although there are probably several mechanisms that lead to restenosis of arteries, an important one is the inflammatory response, which induces tissue proliferation around an angioplasty site. The inflammatory response can be caused by the balloon expansion used to open the vessel, or if a stent is placed, by the foreign material of the stent itself.

Embodiments of the present invention are applicable to treatment of various body lumens with bioabsorbable polymer stents, in particular, treatment of coronary and peripheral disease in coronary arteries and various peripheral vessels including the superficial femoral artery, the iliac artery, and carotid artery. The embodiments are further applicable to various stent types, such as self-expandable and balloon expandable stents. The embodiments are further applicable to various stent designs including scaffolding structures, often formed from tubes, wire structures, and woven mesh structures.

In embodiments of the present invention, a stent can include a plurality of cylindrical rings connected or coupled with linking elements. When deployed in a section of a vessel, the cylindrical rings are load bearing and support the vessel wall at an expanded diameter or a diameter range due to cyclical forces in the vessel. Load bearing refers to the supporting of the load imposed by radial inwardly directed forces. Structural elements, such as the linking elements or struts, are non-load bearing, serving to maintain connectivity between the rings. For example, a stent may include a scaffolding composed of a pattern or network of interconnecting structural elements or struts.

Figure 1:
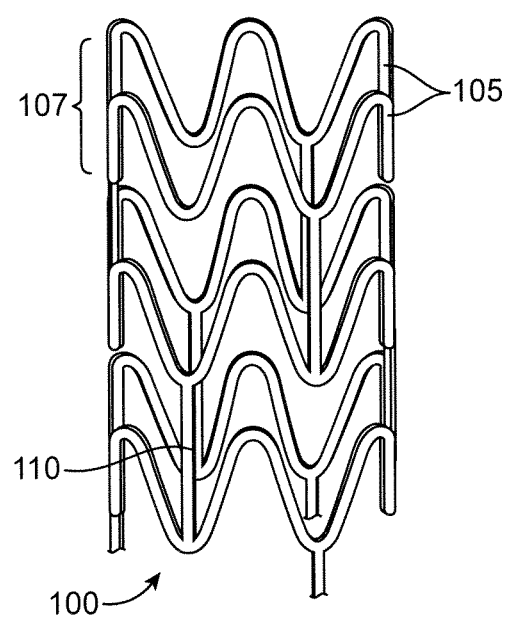
FIG. 1 depicts an exemplary stent scaffolding.

FIG. 1 depicts a view of an exemplary stent 100. In some embodiments, a stent may include a body, backbone, or scaffolding having a pattern or network of interconnecting structural elements 105. Stent 100 may be formed from a tube (not shown). FIG. 1 illustrates features that are typical to many stent patterns including cylindrical rings 107 connected by linking elements 110. As mentioned above, the cylindrical rings are load bearing in that they provide radially directed force to support the walls of a vessel. The linking elements generally function to hold the cylindrical rings together. A structure such as stent 100 having a plurality of structural elements may be referred to a stent scaffolding or scaffolding. Although the scaffolding may further include a coating, it is the scaffolding structure that is the load bearing structure that is responsible for supporting lumen walls once the scaffolding is expanded in a lumen.

The structural pattern in FIG. 1 is merely exemplary and serves to illustrate the basic structure and features of a stent pattern. A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed on a tube or sheet with a technique such as laser cutting or chemical etching. The stent can then be crimped on to a balloon or catheter for delivery into a bodily lumen.

The manufacturing process of a stent scaffolding includes selection of a bioabsorbable polymer raw material or resin. The processing steps for making a stent scaffolding include: melt processing (extrusion) of the resin to form a tube, optional expansion of the tube, laser cutting the tube to form a scaffolding, optional coating of the laser cut scaffolding, crimping the laser cut scaffolding to a reduced diameter over a delivery balloon, packaging the stent and balloon, and radiation sterilization.

The prevailing mechanism of degradation of biodegradable polymer is chemical hydrolysis of the hydrolytically unstable backbone. In a bulk eroding polymer, polymer is chemically degraded throughout the entire polymer volume. As the polymer degrades, the molecular weight decreases. The reduction in molecular weight is followed by a decrease in mechanical properties (e.g., strength) and stent properties. The decrease of mechanical properties is followed by loss of mechanical integrity and then erosion or mass loss. Mechanical integrity is demonstrated cracking and by fragmentation. Enzymatic attack and metabolization of the fragments occurs, resulting in a rapid loss of polymer mass.

The term "molecular weight" can refer to one or more definitions of molecular weight. "Molecular weight" can refer to the molecular weight of individual segments, blocks, or polymer chains. "Molecular weight" can also refer to weight average molecular weight or number average molecular weight of types of segments, blocks, or polymer chains. The number average molecular weight (Mn) is the common, mean, average of the molecular weights of the individual segments, blocks, or polymer chains. Molecular weight is typical expressed in grams/mole which is referred to as "Daltons." It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi Unless otherwise specified, "molecular weight" will refer to number average molecular weight (Mn).

The treatment of artery disease with a stent of the present invention has time dependent properties once it is implanted which enable the treatment and healing of a diseased section of the vessel. In particular, time dependent properties include the molecular weight, the mechanical properties, stent properties (e.g., radial strength), the mechanical integrity, and mass. The treatment process can be related to phases of the degradation schematically illustrated in FIG. 2.

Figure 2:
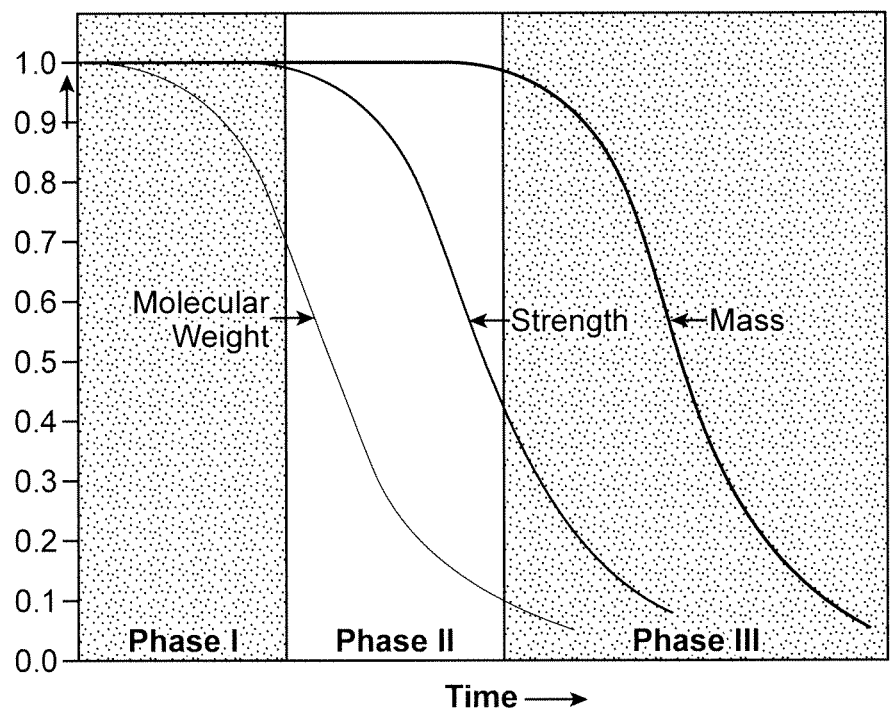
FIG. 2 is a schematic illustrate of the degradation behavior for a bioabsorbable scaffolding in terms of the sequence of molecular weight decrease, loss of strength, and mass loss.

FIG. 2 is a schematic illustrating the life cycle of a poly(L-lactide) scaffolding after in vivo implantation which can be described by the sequence of molecular weight decrease, loss of strength, and mass loss. Pistner H, Bendix D, Muhling J, Reuther J. Poly(L-lactide): a long-term degradation study in-vivo. *Biomaterials.* 1993; 14: 291-298.

This degradation/resorption can further be divided into three phases. During Phase I, molecular weight reduction occurs while neither mechanical strength nor mass is affected. When the molecular weight is sufficiently low enough to impact the scaffolding mechanical properties, the material enters Phase II degradation, in which the scaffold experiences a gradual loss of strength. In Phase III, significant mass loss occurs after hydrolytic chain scission yields water-soluble low molecular weight species.

Among the three phases, Phase I is of particular importance for a bioabsorbable scaffolding treatment. During Phase I, the scaffolding is required to function like a permanent metallic stent to prevent restenosis caused mainly by constrictive remodeling (vessel shrinkage). Ormiston J A, Serruys P W, *Circulation: Cadiovascular Interventions* 2, 255 (2009). As discussed in detail herein, the inventors have found the duration of Phase I, or the time to loss of radial strength, is dependent upon two parameters (see FIG. 8): 1) the degradation kinetics (degradation rate) and 2) the initial molecular weight at a time of degradation t=0 of the scaffolding (Mn (0)). Mn (number-average molecular weight) is employed because it is more relevant to hydrolytic degradation as hydrolysis occurs to each polymer chain. As discussed in detail herein, the inventors have demonstrated that the control of the degradation kinetics can be achieved by controlling the lactide content in the extruded tubes, leading to an in-process lactide content specification. Unless otherwise specified, lactide refers to L-lactide monomer that is not polymerized or chemical bound to other molecules.

In phase 1 of the degradation process, the scaffolding provides the initial clinical need of providing mechanical support to maintain patency or keep a vessel open at or near the deployment diameter. The patency provided by the stent allows the stented segment of the vessel to undergo positive remodeling at the increased deployed diameter and to prevent negative remodeling. Remodeling refers generally to structural changes in the vessel wall that enhance its load-bearing ability so that the vessel wall in the stented section can maintain an increased diameter in the absence of the stent support. A period of patency is required in order to obtain permanent positive remodeling.

During phase I, the bioabsorbable stent's performance effectively mimics the performance of a durable or nonbiodegradable stent in that the bioresorbable scaffold has a high constant radial strength, minimum recoil, good deliverability, and therapeutic agent delivered to abluminal tissue at a controlled rate.

During phase I, the stent inhibits or prevents the natural pulsatile function of the vessel. The stent structure inhibits recoil (e.g., less than 10%) and maintains a circular lumen while the vessel remodels and molds itself to the stented diameter, which corresponds to positive remodeling. Early recoil before sufficient modeling takes place can result in negative remodeling, referring to molding of the stent to a diameter significantly less than the original stented diameter, for example, 50% or less than the original deployment diameter.

At the start of phase II, the radial strength of the stent starts to decrease due to a decrease in molecular weight. The radial strength degrades to the point that the stent can no longer support the walls of the section of the vessel. As the radial strength of the stent decreases, the load of the vessel is gradually transferred from the stent to the remodeled vessel wall which can ideally support itself at the remodeled diameter. Remodeling of the vessel wall continues after loss of radial strength of the stent. In phase II, the stent also begins to lose mechanical integrity. Before the stent loses mechanical integrity, it is desirable for the stent structural elements to become incorporated in the vessel wall by an endothelial layer. The stent then breaks apart which allows vasomotion. The vessel wall continues to remodel as the vessel moves due to vasomotion.

In phase III, the stent eventually erodes away completely leaving a healed vessel with an increased diameter and which can exhibit vasomotion the same or similar to a healthy vessel section.

Poly(L-lactide) (PLLA) is attractive as a stent material due to its relatively high strength and a rigidity at human body temperature, about 37° C. Since it has a glass transition temperature between about 60 and 65° C. (Medical Plastics and Biomaterials Magazine, March 1998), it remains stiff and rigid at human body temperature. This property facilitates the ability of a PLLA stent scaffolding to maintain a lumen at or near a deployed diameter without significant recoil (e.g., less than 10%).

In general, the Tg of a semicrystalline polymer can depend on its morphology, and thus how it has been processed. Therefore, Tg refers to the Tg at it relevant state, e.g., Tg of a PLLA resin, extruded tube, expanded tube, and scaffold.

Degradation profile refers generally to the time dependence or change in the properties of a bioabsorbable stent or scaffolding with time upon implantation in body lumen of an animal or human patient. It can also refer changes in properties with time in vitro. The properties include the molecular weight of the stent body or scaffolding polymer, the strength of the stent body or scaffolding polymer, mass of the stent body or scaffolding, the mechanical integrity of the stent or scaffolding, and the radial strength of the stent or scaffolding.

Two features of a degradation profile that are important for treatment are time to or time of loss of radial strength and the time for complete absorption of the stent or degradation time. The time of loss of radial strength is also referred to the time that a stent maintains radial strength after implantation and is the time period from implantation to the time that the radial strength of the stent starts to lose radial strength.

Ideally, it is desired that once the stent starts to lose radial strength, the bioabsorbable scaffold be absorbed as fast as possible while also meeting all basic safety requirements during its degradation period. Such safety requires can include a gradual disintegration and resorpton that does not allow release of fragment that could cause adverse events such as thrombotic events, or an abrupt release of degradation products that may induce inflammation response. In this way, the stent scaffolding enables the positive remodeling for vessel healing as well as enabling the advantages mentioned herein of a bioabsorbable scaffolding to the greatest extent. Therefore, it is very important not only to develop methods for functional property control at the time of implantation ($T_0$), but also methods for degradation profile control from $T_0$ to complete resorption.

The various embodiments of the present invention include determining properties of a bioabsorbable scaffolding that provide features of the degradation profile that meet required or desired degradation properties for a designated treatment. The scaffolding properties include the initial number average molecular weight, Mn(0) and the scaffolding degradation rate constant. The inventors have found that the degradation rate constant depends on monomer content of the scaffolding, and thus, that the monomer can be used to control the degradation rate constant. The features of the degradation profile include the time to loss of radial strength and the degradation time (time for complete absorption) of the scaffolding. The desired degradation properties include the minimum time of mechanical support or patency time and desired degradation time.

Preclinical and clinical studies of balloon angioplasty have demonstrated that restenosis is caused mainly by early constrictive remodeling (vessel shrinkage) and to a much less degree by hyperplastic healing response*. Mintz G, Popma J, Pichard A, Kent K, Satler L, Wong C D, Hong M, Kovach J, Leon M, *Circulation* 94, 35 (1996); Kimura T, Kaburagi S, Tamura T, Yokoi H, Nakagawa Y, Hamasaki N, Nosaka H, Nobuyoshi M, Mintz G, Popma J, Leon M, *Circulation* 96, 475 (1997); Di Mario C, Gil R, Camenzind E, Ozaki Y, von Birgelen C, Umans V, de Jaegere P, de Feyter P, Roelandt J, Serruys P W, *American Journal of Cardiology*, 75, 772 (1995); Luo H, Nishioka T, Eigler N, Forrester J, Fishbein M, Berglund H, Siegel R, *Arteriosclerosis, Thrombosis and Vascular Biology* 16, 1393 (1966).) The constrictive remodeling can be prevented through implantation of a vascular scaffold to keep the vessel open for a certain period of time. Nobuyoshi et al. studied restenosis rate post-angioplasty at 1 month, 3 months, 4 months, 6 months and 1 year. Nobuyoshi M, Kimura T, Nosaka H, MiokaS, Ueno K, Yokoi H, Hamasaki N, Horiuchi H, Ohishi H, *Journal of the American College of Cadiology* 12, 616 (1988). Using serial angiography, they concluded that the restenosis rate increased remarkably between 1 and 3 months after coronary angioplasty and plateaued thereafter. This finding is in agreement with Serruys et al.'s results that after balloon angioplasty, restenosis occurs mostly within 3 months, and is rarely observed to increase thereafter. Ormiston J A, Serruys P W, *Circulation: Cadiovascular Interventions* 2, 255 (2009); Serruys P W, Luijten H E, Beatt K J, Geuskens R, de Feyter P J, van den Brand M, Reiber J H, ten Katen H J, van Es G A, Hugenholtz P G, *Circulation* 77, 361 (1988).) Hence, to prevent constrictive remodeling and the resulting restenosis, it is desired for a bioabsorbable stent to provide mechanical support to the vessel wall for a minimum of 3 months.

Therefore, for coronary applications, the minimum time period for a stent to provide support (minimum patency period) for positive remodeling is at least about three months. Therefore, the time to loss of radial strength or time radial strength is maintained is desirably at least about three months. For peripheral application, it is expected that the minimum patency period should be somewhat longer, for example, at least about four to five months. For nasal application, the minimum patency period may be shorter, for example, at least about 3 weeks post endonasal frontal sinus surgery. For neural applications, the minimum patency period may be 3 months.

With respect to degradation time, it is desirable for a bioabsorbable stent to have a degradation time of about 18 to 26 months for coronary vascular application, of about eighteen months (e.g., 16-20 months) for a peripheral application (e.g., superficial femoral artery (SFA)), 18 to 24 months for neural applications, and less than a year for nasal applications. It should be appreciated that the methods described herein for controlling the degradation profile and features thereof are generally applicable and not limited to the ranges above.

The various embodiments of the present invention include controlling the degradation profile of a poly(L-lactide) stent, in particular, the time to loss of radial strength and the degradation time. In these embodiments, the degradation profile is controlled by the number average molecular weight at the time of implantation or zero time (Mn(0)) and the monomer content of the finished scaffold, MCs, (i.e., L-lactide) of the poly(L-lactide). Monomer content refers to the content of monomers which are not chemically bonded to the polymer.

The Mn(0) of the scaffolding is the Mn of polymer scaffolding of the final or finished stent product. Final or finished product can refer to the stent or stent scaffolding right after sterilization, any time after sterilization, or immediately before or immediately after delivery in a human patient.

The inventors have found through numerous studies that the degradation profile of poly(L-lactide) is dominantly controlled by Mn(0) and the degradation rate constant of poly(L-lactide). As discussed below, the inventors have found that the degradation rate constant can be controlled by the monomer content in a predictable and consistent manner.

The inventors have recognized that the desired or required properties of a PLLA scaffolding can be predicted using the degradation kinetics of PLLA, in particular, the degradation kinetics of Mn. The inventors have found that degradation profile of the Mn of poly(L-lactide) scaffolds can be approximated by an autocatalytic kinetic relation:

$$\ln [Mn(t)/Mn(0)] = -kt$$

or $$Mn(t)/Mn(0) = \exp(-kt),$$

where k is the degradation rate constant. C. G. Pitt, M. M. Gratzl, G. L. Kimmel, J. Surles, A. Schindler, Biomaterials 2, 215 (1981).

Figure 3A:
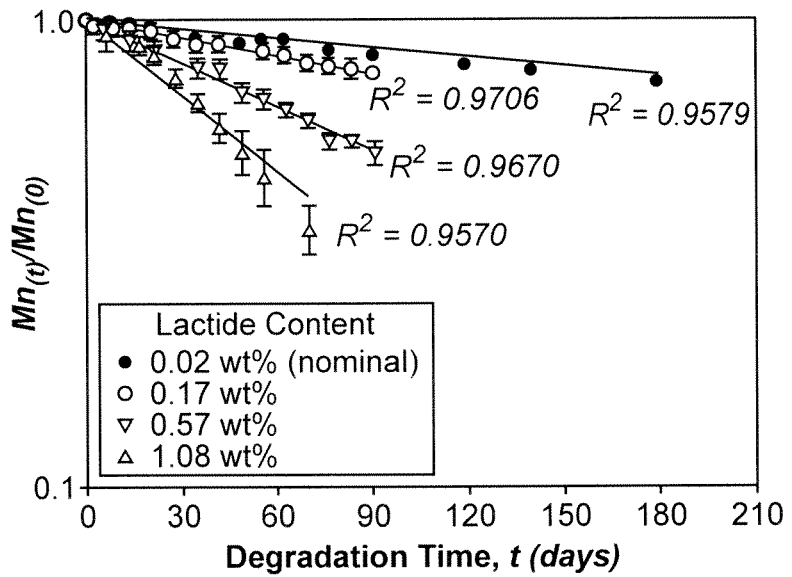
FIG. 3A depicts the degradation profile of PLLA scaffolding for different monomer concentrations.
Figure 3B:
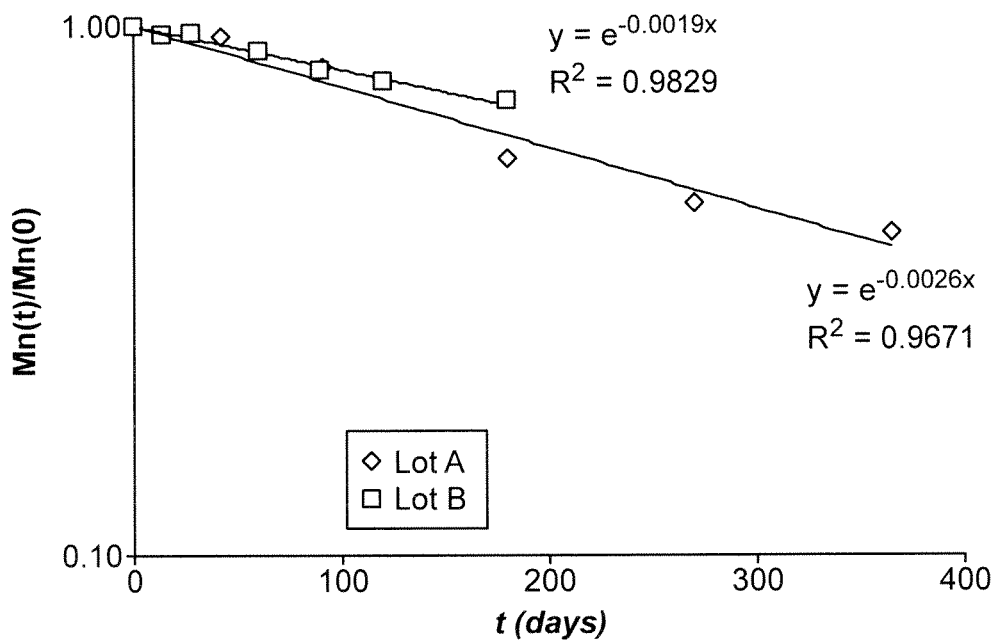
FIG. 3B depicts the degradation profile from in vitro tests for two animal study lots.

The inventors have tested the relation between lactide content in PLLA extruded tubes and the degradation profiles for PLLA scaffolds. FIG. 3A depicts the degradation profile of PLLA scaffolding for different monomer concentrations. FIG. 3B depicts the degradation profile from in vitro tests for two lots of scaffolds used in animal studies which is fit to the kinetic relation above. All sets of data are an excellent fit to the kinetic relation.

Figure 4:
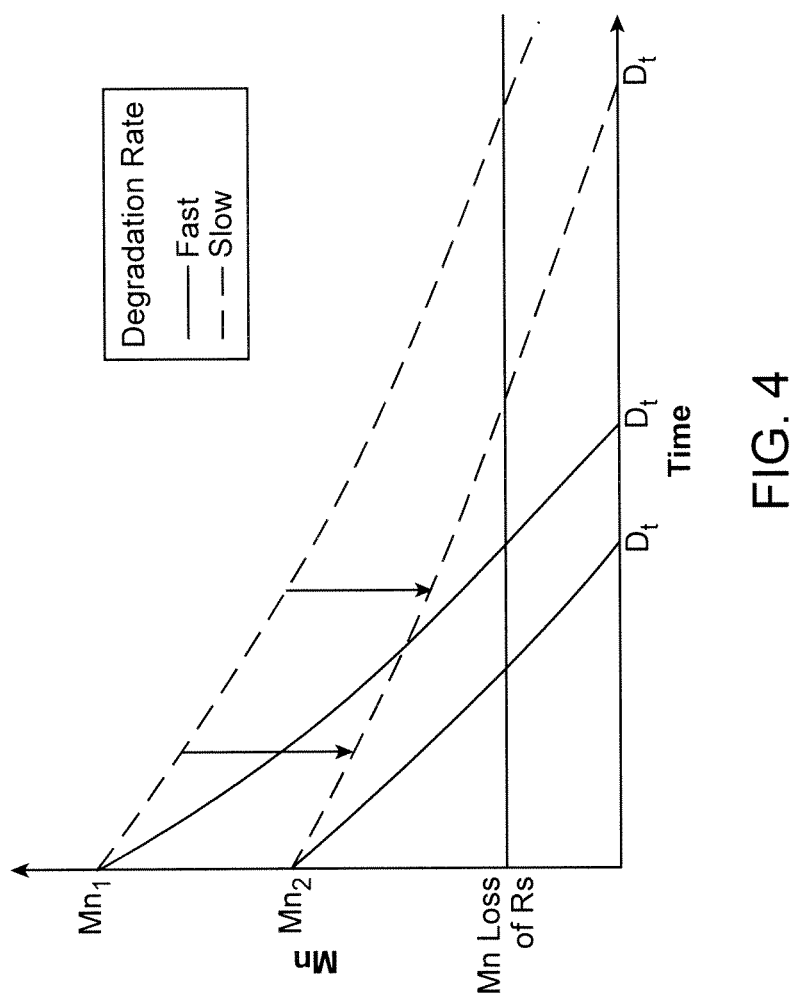
FIG. 4 is a schematic illustration of the dependence found by inventors of the degradation profile and its relevant features on Mn and the degradation rate or rate constant.

With respect to Mn, based on inventors' studies in recent years, it has been found that the Mn of a poly(L-lactide) stent scaffold immediately starts to decrease after scaffold implantation. FIG. 4 is a schematic illustration of the dependence found by inventors of the degradation profile and its relevant features (time to loss of radial strength and degradation time) on Mn and the degradation rate or rate constant. FIG. 4 shows two sets of degradation profiles corresponding to two initial Mn(0)'s. Two degradation profiles are shown for each Mn(0), each with a different degradation rate or rate constant. Thus, FIG. 4 shows the impact of Mn(0) and degradation rate constant on the degradation profile of a bioabsorbable scaffold. For example, at the higher Mn(0), the degradation profile becomes steeper with an increase in the degradation rate constant, resulting in a decrease in the degradation time. FIG. 4 further shows that a decrease in Mn(0) shifts the degradation profile down as shown by the arrows, resulting in a decrease in the degradation time.

The inventors have also found that the change with time of radial strength and scaffold integrity during degradation depends on the scaffold molecular weight. In general, the value of the radial strength and the radial stiffness are not functions of a scaffold material alone. The strength and stiffness (modulus) of a material are distinguishable from the radial strength and radial stiffness since the latter two quantities are stent properties. Stent properties are a complex function of the material of a stent and its geometry, which includes the stent pattern and thickness of structural elements. Thus, the actual values of the radial strength and stiffness depend on material and geometry of the stent.

Figure 5:
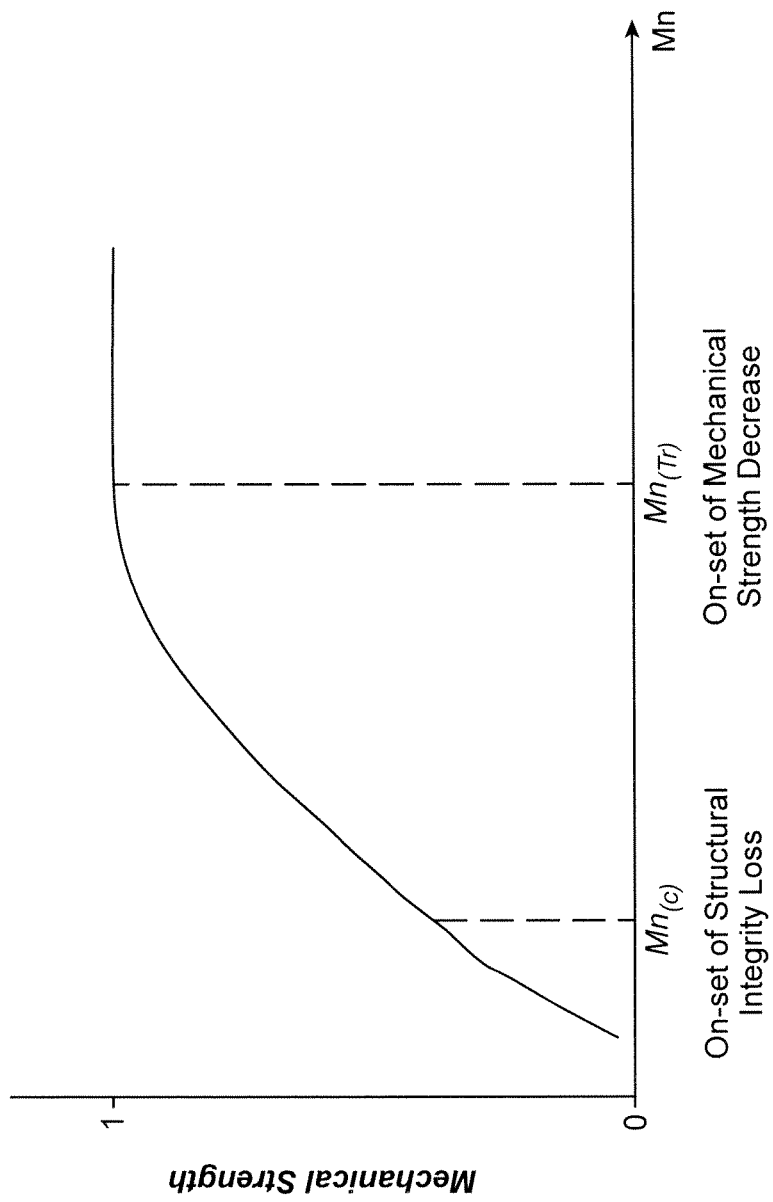
FIG. 5 shows the change in the mechanical strength of the bioabsorbable scaffold as the Mn changes.

Several studies by the inventors have suggested that the onset of desired mechanical strength (e.g., radial strength and tensile strength) loss is associated with a transition molecular weight, Mn,Tr, for the PLLA backbone. FIG. 5 depicts a generic graph of mechanical strength evolution as a function of molecular weight and defines Mn,Tr and Mn,c by their locations on the graph. When the molecular weight is higher than Mn,Tr, mechanical strength is independent of molecular weight. When molecular weight decreases below Mn,Tr, mechanical strength starts to decrease yet retains mechanical integrity until a critical molecular weight, Mn,c, is reached where the bioabsorbable scaffold becomes so brittle that mechanical integrity starts to be lost. Since the decrease of strength is expected to occur prior to the loss of mechanical integrity, to ensure a bioabsorbable scaffolding maintains adequate strength at the desired degradation time point, Mn,Tr may be used for the prediction of a minimum Mn(0).

For a bioabsorbable PLLA scaffold, the Mn,Tr is 47 kDa (Example 4). The Mn,Tr is found to be independent of the degradation rate constant. The time to reach Mn,Tr corresponds to the time of loss of radial strength. Mn,Tr is the lower bound of Mn at a desired time of patency. If Mn of a scaffolding falls below Mn,Tr before the desired patency time, the scaffolding has not supported the lumen long enough for positive remodeling to take place.

Referring again to FIG. 4, the time for loss of radial strength and degradation time (Dt) depend on the Mn(0) and degradation rate. As the Mn(0) decreases from Mn1 to Mn2, both the time for loss of radial strength and the degradation time decrease. Additionally, as shown by the profiles for Mn1 and Mn2, as the degradation rate increases, the degradation profile for Mn becomes steeper which decreases the time for loss of radial strength and the degradation time.

The inventors found that as the PLLA scaffolding further degraded to an Mn of 30 kDa, the scaffold started to lose its mechanical integrity. The Mn at the onset of loss of mechanical integrity is referred to as Mn,c.

As indicated above, there is a desired minimum time of patency for treatment with a stent to provide positive remodeling. Therefore, a bioabsorbable scaffold should have a degradation profile with a Mn at the desired minimum time of patency greater than the Mn,Tr. The Mn,Tr represents a lower bound for Mn at the desired minimum time of patency. For a coronary artery lesion treatment, the minimum time of patency is about three months in order to meet basic safety requirement of scaffold design.

Figure 6:
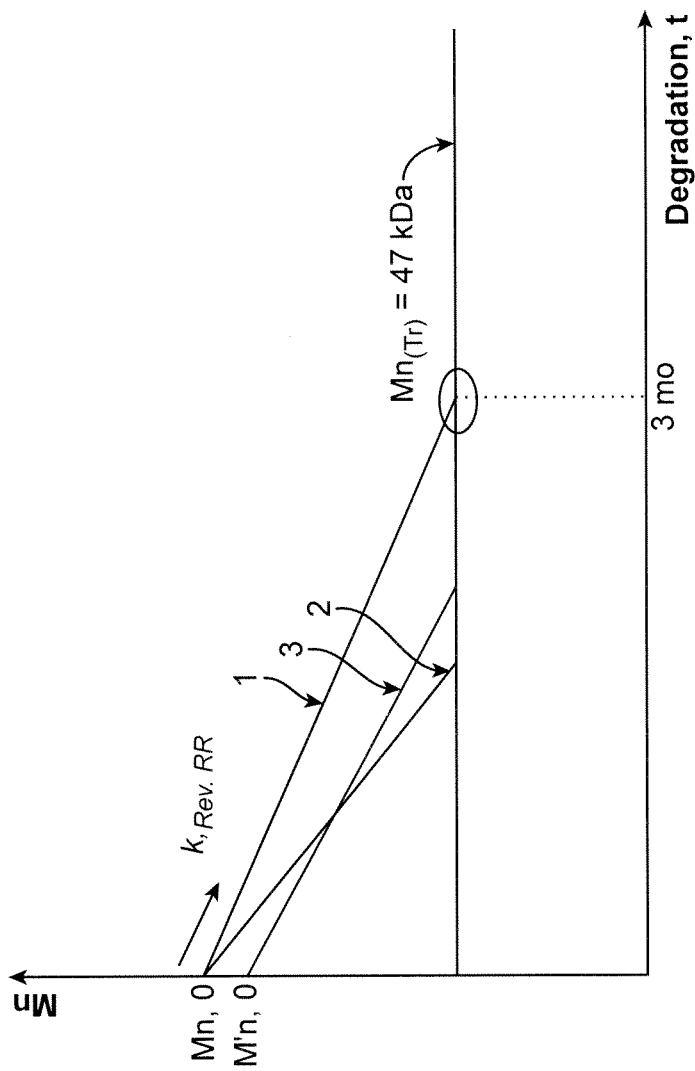
FIG. 6 depicts three degradation profiles with profile 1 exhibiting an Mn at three months equal to the three month required patency for coronary treatment.

FIG. 6 depicts three degradation profiles of a PLLA scaffolding, for example, with profile 1 having a Mn at 3 months equal to Mn,T, which is acceptable for coronary treatment. Profile 2 has the same Mn(0) as profile 1, but has a higher degradation rate or rate constant which results in a Mn at the desired time of patency lower than Mn,T. Profile 3 has the same degradation rate or constant with a lower Mn(0) than profiles 1 and 2. As a result, the Mn at the desired patency time is less than Mn,T. It can further be appreciated that a change in either or both the Mn(0) or the degradation rate will also change the degradation time of the bioabsorbable scaffold.

Therefore, the inventors have found that the Mn(0) and the degradation rate can be adjusted to obtain a degradation profile that meets the requirements of a particular treatment, e.g., desired time of patency, time of loss of structural integrity, and degradation time.

As indicated above, the inventors found that the degradation rate constant can be controlled by the monomer content in the bioabsorbable scaffold in a predictable and consistent manner. Specifically, the inventors found that the degradation rate constant shows a linear relationship to the lactide monomer content in a PLLA scaffold.

The inventors have found that pre-clinical studies using porcine models have indicated an increasing dependence of the scaffold integrity on the in vivo molecular weight declining kinetics. The inventors have further found that corresponding in vitro studies demonstrated that the on-set of radial strength decrease was observed earlier on the samples associated with higher in vitro degradation rate constant (k). Therefore, a well-defined manner of molecular weight loss is crucial for the control of degradation and resorption behavior of a bioabsorbable scaffold. A comparison by the inventors of in vivo and in vitro results showed that the molecular weight data at each time point during early stage degradation was similar between both models. This finding echoed findings in literature references (Weir N. A., Buchanan F. J., Orr J. F., Diskson G. R. "Degradation of poly-L-lactide. Part 1: in vitro and in vivo physiological temperature degradation", *Proceedings of the Institution of Mechanical Engineers. Part H: Journal of Engineering in Medicine* 218, 307-319 (2004); Hayashi T. "Biodegradable polymers for biomedical uses", *Progress in Polymer Science* 19, 663-701 (1994)) that early-stage poly(L-lactide) degradation in vivo was mainly due to simple hydrolysis with minimal enzyme activities Hence, the use of in vitro method as a surrogate for in vivo degradation behavior is applicable.

Lactide is the dominant thermal breakdown by-product of the polymer during melt extrusion processing. By tracking the lactide content during different downstream processing steps of extruded tube lots, the inventors confirmed, as shown by Example 1, that extrusion was the most significant contributor to the lactide content. Thus, lactide monomer in the resin and lactide generated during extrusion are primarily or completely the source of monomer in the finished stent scaffolding. The inventors have also found, as shown in Example 2, that at lactide content levels of ≤0.5 wt %, controlling lactide content in extruded tubes is sufficient to control lactide content in a finished scaffolding.

The inventors have studied the degradation behavior of extruded tubing lots with different lactide content with in vitro studies to test the predictive ability of the degradation kinetic model $$\ln\left(\frac{M_n(t)}{M_n(0)}\right) = -kt.$$

FIG. 3A includes lines that are an exponential regression based on the kinetic model. Each data point represents n=6 and error bars represent one standard deviation. $R^2$ (Coefficient of determination) denotes the goodness of the model fit. The exponential regression is used to determine degradation rate constant, k, according to the model.

Figure 7:
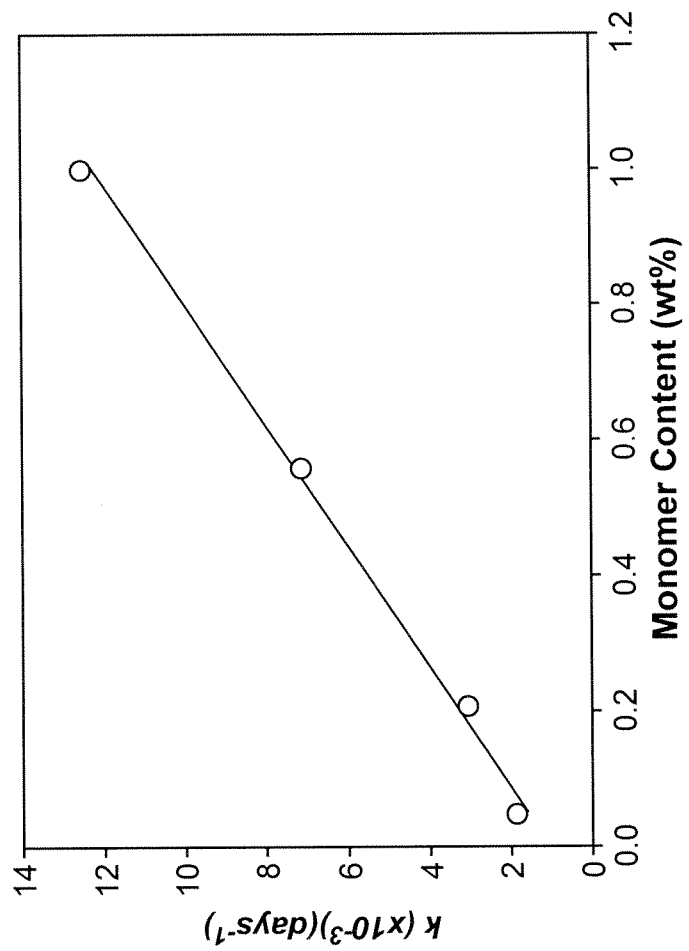
FIG. 7 depicts the degradation rate constant (k) as a function of lactide content calculated from the linear regression plots in FIG. 3A.

The autocatalytic model was employed to calculate the degradation rate constant (k) for each group in FIG. 3A. FIG. 7 depicts the degradation rate constant (k) as a function of lactide content calculated from the linear regression plots in FIG. 3A. FIG. 7 reveals a linear positive dependence of the in vitro degradation rate constant (k) on the lactide content. The obtained model (using Sigma Plot) is demonstrated by the relation:

$$k(\times 10^{-3}) = 10.080[LA] + 1.5131$$

where k is the first-order rate constant (days$^{-1}$) and [LA] is the lactide content in the extruded tubes (wt %). This confirms that the higher the initial lactide content in the extruded tubes, the faster the scaffolding samples degraded. Moreover, the linear correlation can be utilized to predict the degradation kinetics from a given initial lactide content within the range of ca. 0.02 wt % to ca. 1.08 wt %.

As a result of various degradation kinetics induced by different lactide content, the temporal radial strength progression during degradation is expected to be impacted as well. By tracking the radial strength progression over degradation time, the inventors also showed that, higher lactide content shortened the duration that radial strength was maintained in finished scaffolds (FGs) (Example 3).

Figure 8:
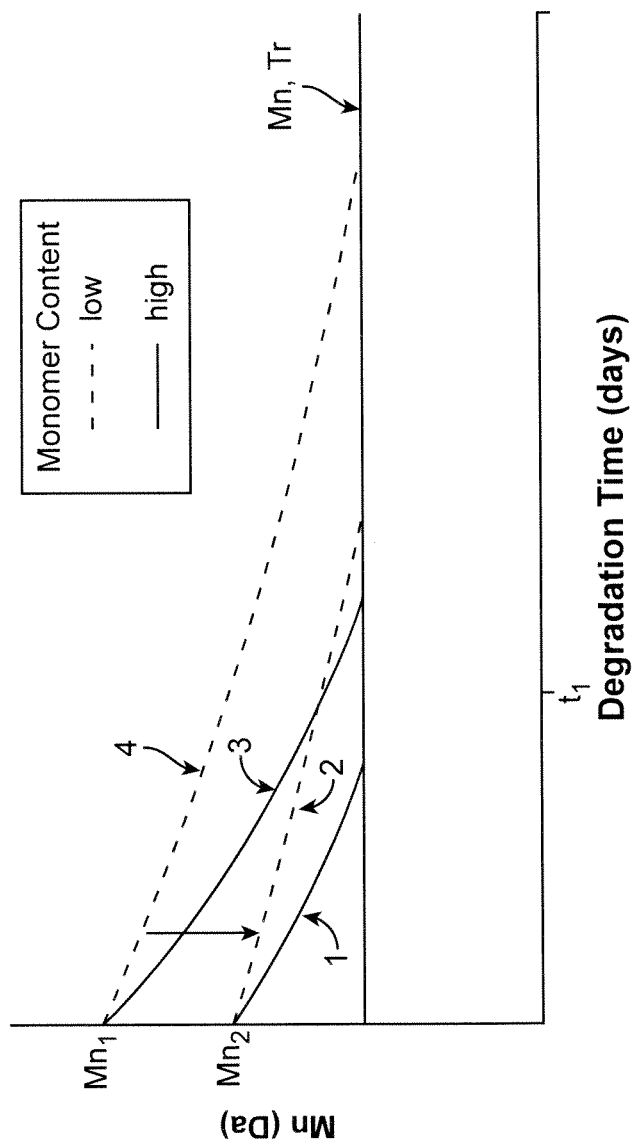
FIG. 8 depicts degradation profiles for a bioabsorbable scaffold with two different starting Mn and each with two different monomer concentrations.

FIG. 8 illustrates the dependence of the degradation profile and its relevant features on Mn and the monomer concentration. FIG. 8 shows two sets of degradation profiles corresponding to two initial Mn(0)'s, Mn1 and Mn2. Two degradation profiles are shown for each Mn(0), corresponding to two different monomer concentrations. Thus, FIG. 8 shows the impact of Mn(0) and monomer concentration on the degradation profile of a bioabsorbable scaffold. For Mn1 and Mn2, the degradation profile becomes steeper with a higher monomer concentration. FIG. 8 further shows that a decrease in Mn(0) shifts the degradation profile down as shown by the arrows. Thus, the inventors have found that increasing L-lactide concentration shortens the duration that radial strength is maintained by a stent scaffolding.

FIG. 8 can be used to illustrate adjustment or selection of the monomer concentration to obtain a desired time of loss of radial strength and degradation time. For example, if the required time of patency is t1, then profile 1 is not acceptable since Mn falls below Mn,Tr, thus losing radial strength, prior to t1. Profiles 2-4 are acceptable since Mn is greater than Mn,Tr at t1, thus the time of loss of radial strength for each occurs after t1. Thus, as compared to profile 1, a higher Mn(0) (e.g., profile 3), lower monomer concentration (profile 2), or both should be selected or adjusted. Furthermore, the degradation time of profile 4 may be higher than desired for coronary treatment, for example, 5 years. In this case, a lower Mn (e.g., profile 2), higher monomer concentration (e.g., profile 3), or both can be selected to obtain a lower degradation time while also obtaining an acceptable time of loss of radial strength.

Monomer content can be controlled in several ways. These include selection of a commercial resin with a desirable level of monomer concentration. In addition, extrusion conditions can be controlled to reduce monomer generation which tends to increase as extrusion temperature increases. Additionally, monomer concentration can be increased through addition of monomer to a scaffolding polymer, for example, in the extrusion step.

Although the various embodiments of the present invention have been applied to PLLA scaffolds with two different scaffolding designs, the methods can be applied generally to other types of bioabsorbable polymers and other scaffolding designs. The methods of controlling the degradation profile of a bioabsorbable scaffold are applicable to various types of treatment (e.g., coronary, SFA, neural, nasal) and different scaffold designs. The Mn(0) and initial monomer content of the scaffold can be used to control the degradation profile which meets the specifications of a type of treatment. The magnitude of the radial strength to support of a lumen for each case can be obtained through the type of polymer selected and scaffold geometry (e.g., pattern structural element thickness). As discussed above, there may be preferred or required degradation profile features for a bioabsorbable stent scaffolding including a selected degradation time or range and a time that the scaffolding maintains patency of a lumen. The methods of making a stent scaffolding may then include determining an Mn(0), an MCs, or both that provides the desired degradation profile feature(s). The methods further include fabricating a stent scaffolding such that the finished stent scaffolding has the determined Mn(0), MCs, or both.

The predictive model based upon the autocatalytic mechanism of PLLA degradation, may be utilized to obtain the minimum initial Mn at degradation t=0:

$$\ln Mn(0) = \ln Mn, Tr + k_r t \qquad (1)$$

where $k_r$ is the reference degradation rate constant (days$^{-1}$), Mn(0) is the initial number average molecular weight, and Mn,Tr is the mechanical strength transition number average molecular weight at the minimum required degradation time period t (days) for product safety. The minimum Mn(0) is the lowest initial Mn of a scaffold that will maintain patency for a desired minimum patency time (e.g., 3 months). In order to obtain the predicted Mn(0), each parameter (Mn,Tr, $k_r$, and t) is determined or specified.

As discussed above, the degradation rate constant and lactide content follow a linear regression, represented by:

$$k(\times 10^{-3}) = 10.080[LA] + 1.5131 (R^2 = 0.9988)$$

where k is the degradation rate constant (days$^{-1}$), LA is the initial lactide content in the extruded tubes (wt %). For a lactide content specification of ≤0.2 wt % in the extruded tubes, the fastest possible degradation rate constant, calculated from the above equation, is $3.53 \times 10^{-3}$ days$^{-1}$. For a given pair of Mn,Tr and t, it can be seen from Eq. 1 that faster degradation rate constant requires higher Mn(0); hence, $3.53 \times 10^{-3}$ days$^{-1}$ is chosen as the reference degradation rate constant ($k_r$), as it represents the worst case scenario.

Table 2 summarizes the aforementioned parameters. By applying these parameters to Eq. 1, a minimum initial Mn of 66 kDa is obtained. Hence, an exemplary molecular weight may be Mn(0)≥66 kDa for a lactide content of 0.02 wt %. As discussed previously, this molecular weight is considered as the sum of the PLLA backbone and the PDLLA coating polymer.

TABLE 1

Summary of parameters for the predictive model

| Parameters | Value |
|---|---|
| T | 3 months |
| $Mn,_{Tr}$ | 47 kDa |
| $k,_r$ | $3.53 \times 10^{-3}$ days$^{-1}$ |

In other embodiments of determining Mn(0), the method of making a stent scaffolding can include determining an Mn(0) that provides a desired minimum time of patency. The method can include determining an Mn,Tr of the bioabsorbable stent made from the bioabsorbable polymer, which for a PLLA scaffold is about 47 kDa. The method then includes determining Mn(0) that provides an Mn at the desired minimum patency time equal to the Mn,Tr. A stent scaffolding can be made from the bioabsorbable polymer that has a Mn(0) greater than or equal to the determined Mn(0). The determined Mn(0) can be found from a degradation kinetic model of the bioabsorbable polymer.

Figure 9:
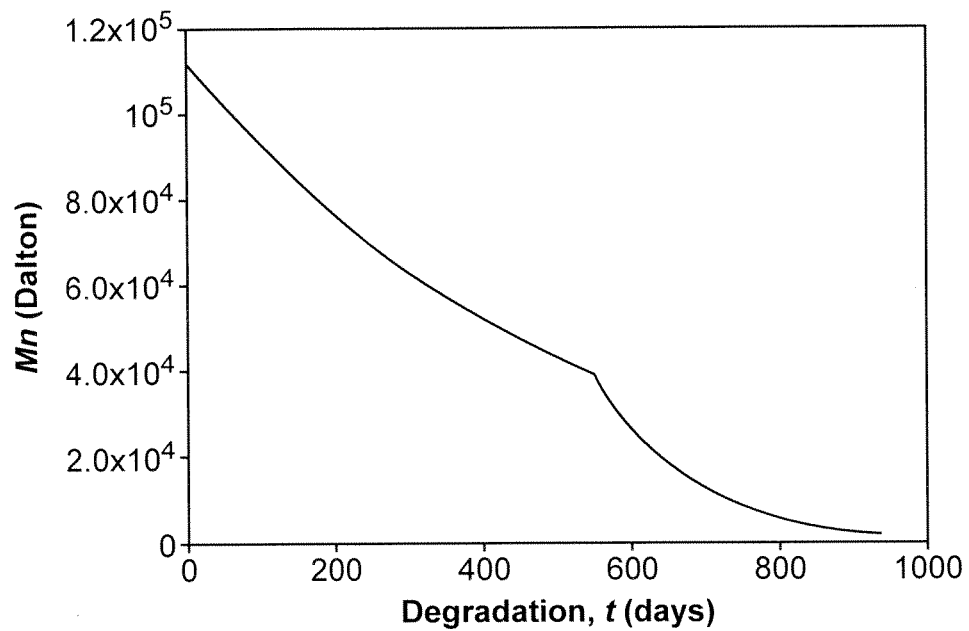
FIG. 9 depicts the Mn vs. time for a PLLA scaffolding.

Based on data obtained from long term in vitro degradation study, the Mn of a PLLA scaffolding with a Mn 110 kDa and L-lactide monomer content of 0.02% or less in the PLLA backbone. The scaffolding has a degradation time may be as long as 29 months as shown in FIG. 9.

Two exemplary modifications include (1) a lactide content of 0.1% or less and (2) lactide content of 0.2% or less. The Mn(0) that provides a selected time that radial strength is maintained or time to loss of radial strength can be determined from the kinetic model.

Figure 10:
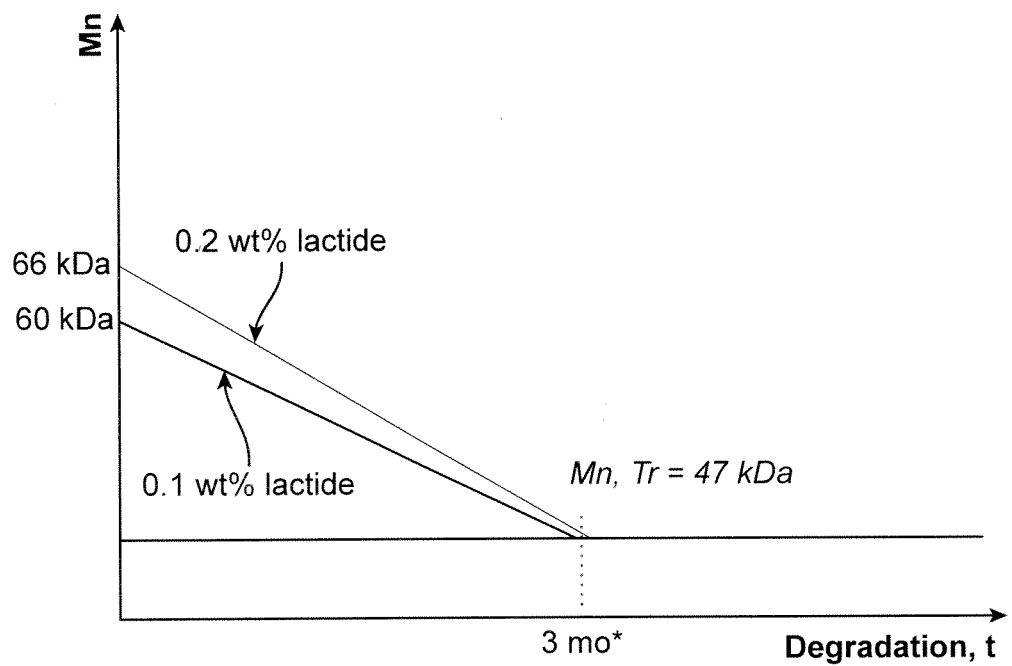
FIG. 10 depicts Mn vs. time of degradation for the two modifications of the PLLA scaffold.

For exemplary modification (1), an Mn(0) of at least 60 kDa would provide radial strength maintained at least 3 months after implantation and its total degradation time would be expected within just 18 months. For exemplary modification (2), an Mn(0) of at least 66 kDa would provide the same results. FIG. 10 depicts Mn vs. time of degradation for the two modifications of the PLLA scaffold: (1) 0.1 wt % Lactide and Mn(0)=60 kDa (2) 0.2 wt % Lactide and Mn(0) =66 kDa.

In certain embodiments, a method of making a stent can include determining Mn(0) that provides desired degradation profile features. The Mn(0) that is determined is for a polymer with a particular degradation rate or rate constant which the inventor found depends on the monomer content. Therefore, the Mn(0) corresponds to a given monomer content.

In some of these embodiments of determining Mn(0), a desired degradation time or range is selected and then a Mn(0) or range of Mn(0) for the stent scaffolding that provides the degradation time or range for a finished stent scaffolding is determined. A stent scaffolding can then be made from the bioabsorbable polymer such that the stent scaffolding has a Mn(0) within the determined range of Mn.

In these embodiments, the determined range of Mn(0) may be determined from a degradation kinetic model of the bioabsorbable polymer. A hydrolytic degradation model for aliphatic polyesters having the form $$Mn(t)=Mn(0)\exp(-kt),$$

where Mn(t) is the number average molecular weight at time t, Mn(0) is the number average molecular weight at t=0, and k is the hydrolytic degradation rate constant. Pitt, C. G., J. of Applied Polymer Science 26, 3779-3787 (1981); Pitt, C. G., Biomaterials 2, 215-220 (1981); Weir, N. A., Proceedings of the Institution of Mechanical Engineers, Part H: J. of Engineering in Medicine 218, 307-319 (2004); Weir, N. A., Part H: J. of Engineering in Medicine 218, 321-330 (2004). The assumptions inherent in the model are reasonable provided that the mass loss has not occurred, since mass loss would affect the concentrations of water and carboxylic end groups in the sample. The equation can also be written as:

$$\ln [Mn(t)/Mn(0)]=-kt.$$

Therefore, by representing data for Mn(t)/Mn(0) versus t on a log-linear plot, the hydrolytic degradation rate constant may be inferred from the slope of the connecting points. The rate constant, k, can be found, for example, from in vitro or in vivo degradation data for the polymer with the given monomer content.

In certain other embodiments, the method of making a stent can include determining MCs that provides desired degradation profile features. The MCs that is determined is for a polymer with a particular Mn(0).

In some of these embodiments of determining MCs, a desired degradation time or range is selected and then a range of MCs that provides the degradation time range is determined. A stent scaffolding is then made from the bioabsorbable polymer such that the MCs is within the determined range. The determined range of MCs can be found from a degradation kinetic model of the bioabsorbable polymer. For example, for PLLA, the rate constant, k, can be found from Mn(t)/Mn(0)=exp(-kt). The MC(0) can then be determined from in vitro degradation data such as that shown in FIGS. 7A-B.

In other embodiments of determining MCs, a desired minimum patency time is selected and then an Mn,Tr of the bioabsorbable stent is determined. An MC,Tr is then determined that provides an Mn at the desired minimum patency time that is equal to the Mn,Tr. A stent scaffolding can then be made from the bioabsorbable polymer such that the MCs is less than or equal to the determined MCs.

The determined MCs can be found using a degradation kinetic model of the bioabsorbable polymer. For example, for PLLA, the rate constant, k, can be found from Mn(t)/Mn(0) =exp(-kt). The MCs can then be determined from in vitro degradation data such as that shown in FIGS. 7A-B.

In the embodiments discussed above, a Mn(0) or MCs is determined for a bioabsorbable polymer scaffolding that provides degradation profile parameters and a stent scaffolding may then be made having the Mn(0) and MCs. Embodiments of present invention include steps for making a stent scaffolding with the determined Mn(0) and MCs.

In extrusion, a polymer is processed above its melting temperature (Tm). The higher the Mn of the resin, the higher the temperature that is required for processing in a extruder since the viscosity of the polymer melt increases with temperature. However, monomer generation increases with temperature and the Mn drop increases with temperature. Exemplary melt processing of a PLLA resin can be performed with a ¾" single screw extruder. For a resin with a Mn of about 350 kDa, the processing temperature is 200-210° C. and the residence time is 8-10 min. The tube is quenched in a room temperature water bath as it exits the die. The extruder barrel pressure is about 2000 psi. The post-extrusion degree of crystallinity is about 10%-15%.

For coronary applications, a polymer tube for use in manufacturing a stent can have an outside diameter of 2-4 mm. For SFA applications, the outside diameter is larger, for example, 4-9 mm. Diameters outside these ranges are also possible. The wall thickness of the polymer tube can be 0.05-3 mm, however, the present invention is applicable to tubes with a wall thickness less than 0.05 mm and greater than 3 mm.

Prior to laser cutting, the tube may be radially expanded to increase its radial strength, which can also increase the radial strength of the stent. The tube can also be axially elongated or extended as well during the expansion process. The radial expansion process tends to preferentially align the polymer chains along the hoop direction which results in enhanced radial strength. The radial expansion step may be crucial to making a stent scaffolding with thin struts that is sufficiently strong to support a lumen upon implantation.

The tube is radially expanded by heating the tube to a temperature between Tg and the melting point of the polymer. Upon expansion the tube is cooled to below the Tg of the polymer, typically to ambient temperature, to maintain the tube at an expanded diameter. The tube is expanded and then cooled at a non-equilibrium rate which then maintains the tube at an expanded diameter. The percent radial expansion may be between 200 and 500%. The percent radial expansion is defined as RE %=(RE ratio−1)×100%, where the RE Ratio=(Inside Diameter of Expanded Tube)/(Original Inside Diameter of the tube). The percent of axial extension that the polymer tube undergoes is defined as AE %=(AE ratio−1)×100%, where the AE Ratio=(Length of Extended Tube)/(Original Length of the Tube).

The tube may be radially expanded by blow molding the tube inside of a glass mold. The tube is heated and expands to the inside diameter of the mold. For example, a heating nozzle blows warm air on the mold as a nozzle translates along length of mold and the tube expands as nozzle translates. The tube may also be in axial tension resulting in axial elongation. In an exemplary embodiment, the tube is expanded from 0.018"ID/0.056"OD to 0.072"ID/0.084"OD, with 350% radial expansion (RE) and 50% longitudinal stretch, where RE=[(outer diameter)$_{finish}$/(outer diameter)$_{start}$−1]×100. For an exemplary PLLA tube, the tube may be heated to about 70 to 110° C. during expansion.

A stent pattern is cut into the expanded tube, for example, by laser machining. The expansion of the tube decreases the wall thickness of the tube. For a coronary stent, the width and thickness of the stent can be, for example, between 140-160 microns. For an SFA stent, the width and thickness may be between 180 and 230 microns.

After cutting a stent pattern into the expanded tube, the stent scaffolding may then be optionally coated with a drug delivery coating which can include a polymer and a drug. An exemplary stent may include a PLLA scaffolding and a coating composed of poly(DL-lactide) and everolimus, for example, in a 1:1 ratio by weight.

In order to make the stent ready for delivery, the stent is secured to a delivery balloon. In this process, the stent is compressed to a reduced diameter or crimped over the balloon. In an exemplary embodiment, the stent is crimped from a cut diameter to a crimped diameter (e.g., from 0.136" to 0.047") in a multi-step process with dwell periods between each diameter reduction. The crimping temperature of the stent can be greater than ambient, for example, about 48° C. or slightly less than Tg for PLLA. A sheath may be placed over stent immediately after crimping to prevent recoil. The stent may then be placed in a pouch which is sealed.

The stent may then be subjected to terminal sterilization after crimping and packaging the crimped stent. Terminal sterilization refers to a final sterilization step in the manufacture of a stent, for example, exposure of the stent to radiation such as e-beam or gamma radiation. Typically, a stent is sterilized in one step, for example, one pass or multiple passes of radiation with no intervening steps. Therefore, the terminal radiation step may be the only sterilization step. No additional radiation exposure occurs after terminal sterilization. The terminal sterilization is typically performed for a stent after crimping and packaging, however, it can be performed, prior to either one or both crimping or packaging.

The packaged stent and catheter are sterilized to reduce the bioburden of the stent and delivery system to a specified level. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product, such as a stent, to be used in the body's fluid path is considered a Class III device and requires an SAL of 10-6. SAL's for various medical devices can be found in materials from the Association for the Advancement of Medical Instrumentation (AAMI) in Arlington, Va.

The sterilization can be performed by exposing the stent and catheter to radiation, for example, electron beam (e-beam), gamma ray, and x-ray sterilization. A sterilization dose can be determined by selecting a dose that provides a required SAL. A sample can be exposed to the required dose in one or multiple passes. An exemplary radiation dose for sterilization of a stent may be 20-35 kGy.

The resin has a molecular weight, Mn,r, and monomer content, MC,r, prior to any processing steps. As stated above, both Mn and MC change during the manufacturing process. The Mn decreases significantly during extrusion and radiation sterilization. The higher the extrusion temperature, the greater is the decrease in Mn. The higher the radiation dose, the greater is the decrease in Mn. For example, a PLLA resin with a Mn of 350 kDa with an extrusion temperature of 215° C. results in an extruded tube with a Mn of 250 kDa. A PLLA stent scaffolding with Mn=250 kDa before e-beam sterilization decrease to a Mn between 90-100 kDa after a radiation does of 27.5 kDa.

MC, as indicated above, can increase during extrusion. The higher the extrusion temperature, the greater is the monomer generation. The Mn,r, MCr in combination with processing parameters, in particular, the processing parameters of extrusion and radiation sterilization may not provide a Mn(0) with a desired degradation profile.

For example, the Mn,r, MCr, and processing parameters may result in a stent scaffolding with a Mn(0) greater than the Mn(0) that provides the desired degradation profile, i.e., the time that maintains radial strength and/or the degradation time is longer than desired. For example, a scaffolding made from a PLLA resin with Mn=365 kDa and LLA monomer content of about 0.1 wt % is processed using the exemplary processing conditions disclosed above to result in a finished PLLA scaffolding with an Mn=100-110 kDa. The degradation time of this stent scaffolding is approximately 2.5 to 3 years, which may be acceptable, but a shorter time may be desired for coronary as well as other applications.

When the Mn(0) is greater than is desired, in certain embodiments, the Mn can be adjusted during processing to provide an Mn(0) that provides the desired processing parameters. In particular, the Mn of the bioabsorbable polymer can be decreased through exposure to radiation, for example, e-beam or gamma radiation. The use of e-beam radiation to modify molecular weight is accomplished by altering the electron beam dose to the PLLA scaffold to achieve a desired molecular weight or Mn of the radiated scaffold. The effect of e-beam is dominated by chain scission of the PLLA molecules, which lowers the molecular weight. A relationship exists between the e-beam dose and the resultant molecular weight to the extent that e-beam can be used to control molecular weight once the initial molecular weight of the scaffold is known. Thus, a wide range of desired starting molecular weights (below the initial molecular weight) can be established by varying the E-beam dose to the scaffold.

In the above embodiments, methods are disclosed for determining a Mn(0) that provides a desired degradation profile, in particular, degradation time and a patency time for a scaffolding. With respect to patency time, the Mn(0) is determined that provides a time of loss of radial strength in the range of a desired patency time.

In certain embodiments, e-beam radiation may be utilized to adjust the Mn to obtain the Mn(0) that is found to provide the desired degradation properties such as the time that the scaffold maintains radial strength while degrading and thus the degradation time of the scaffold.

In some embodiments, the radiation dose at the terminal radiation sterilization step is adjusted to reduce the Mn after crimping to the Mn(0) that provides the desired degradation profile. In such an embodiment, the dose of the radiation required to reduce the Mn after crimping to the desired Mn(0) may be determined from the relationship between dose and Mn determined experimentally or empirically. In an exemplary embodiment, a initial Mn of a PLLA scaffolding after crimping is approximately 250 kDa. The time of loss of radial strength may be reduced to 2.5 or 3 months by determining the Mn(0) corresponding to this time of loss, as disclosed above. Then the required dose to reduce the Mn after crimping to this Mn(0) is found from the radiation dose vs. Mn relation. For example, the e-beam dosage can be adjusted from 31 kGy to 75 kGy to achieve the desired Mn(0).

The inventors have determined that a scaffolding with a Mn(0) of about 70 kDa will provide a degradation time of less than 18 months and the time to loss of radial strength is at least 3 months. Thus, the radiation dose at terminal sterilization can be adjusted to reduce the Mn to about 70 kDa.

In other embodiments, in addition to the terminal radiation step, the Mn can be adjusted with radiation at one or more points in the manufacturing process to achieve a scaffolding with an Mn(0) that provides the desired degradation profile. The advantage of adjusting the molecular weight at more than one step over a single radiation exposure at terminal sterilization is that each exposure can be a lower dose than a single exposure. The lower radiation dose may reduce any potential adverse effects of high radiation doses, such as the high temperature which can cause the scaffolding polymer to change the mechanical properties of the scaffolding.

In some embodiments, the stent scaffolding is exposed to radiation at only one other point in manufacturing. In other embodiments, the stent scaffolding is exposed to radiation at two or more points in manufacturing in addition to terminal stabilization. In these embodiments, the stent scaffolding can be exposed to radiation after laser cutting and before crimping, after laser cutting and before coating and crimping, after coating and before crimping, after expansion and before laser cutting, or after extrusion and before expansion.

In some of these embodiments, the radiation dose at terminal stabilization is 20-31 kGy. The radiation dose(s) prior to terminal sterilization between manufacturing steps is then adjusted so that the Mn of the scaffolding after the terminal stabilization is at the desired Mn(0). In an exemplary embodiment, the additional radiation exposure step is performed only between laser cutting and crimping, in addition to terminal sterilization of 20-35 kGy. The radiation dose between laser cutting and crimping may be adjusted to obtain a desired Mn(0) after terminal sterilization. This radiation dose may be 6-50 kGy. The radiation dose will depend primarily on the Mn and the monomer content. For example, for a PLLA scaffold with a Mn of about 250 kDa and monomer content of about 0.1 wt % after laser cutting, the radiation dose can adjusted to obtain a scaffolding after terminal sterilization of 60 kDa with a degradation time of about 18 months and loss of radial strength at about 3 months.

In certain embodiments, pre-degradation of a PLLA scaffold may be used to adjusting (decrease) the Mn to obtain the Mn(0) that provides the desired degradation properties. The method includes adjusting the PLLA scaffold degradation properties by hydrolytically pre-degrading the scaffolds. The pre-degradation causes a decrease in the Mn of the scaffold. The method may include exposing the scaffold to a fluid for a period of time that causes hydrolytic degradation to the polymer of the scaffold. In such embodiments, a scaffold may be exposed to the pre-degradation fluid by spraying the fluid on the scaffold or immersing the scaffold in the fluid.

The pre-degradation fluid may be water or a water-based fluid. The pre-degradation fluid may be fluid that mimics as closely as possible the in vivo degradation of the scaffolding. A fluid may be used that allows very little change in pH as the scaffolding is pre-degrading, such as a buffer solution. A buffer solution is an aqueous solution including a mixture of a weak acid and its conjugate base or a weak base and its conjugate acid. It has the property that the pH of the solution changes very little when a small amount of strong acid or base is added to it. This is important since hydrolytically degradable aliphatic polymers such as PLLA have acidic degradation products which can cause the pH at or local to the degrading polymer to decrease. Buffer solutions are used as a means of keeping pH at a nearly constant value in a wide variety of chemical applications.

In some embodiments, a phosphate buffered saline (PBS) solution is used. PBS is a water-based salt solution containing sodium chloride, sodium phosphate, and (in some formulations) potassium chloride and potassium phosphate.

Further, in such embodiments, the scaffold may be pre-degraded after a selected step(s) of the manufacturing process. In some embodiments, the scaffold is pre-degraded after laser cutting and before coating. In other embodiments, the scaffold is pre-degraded after coating and before crimping.

In other embodiments, the pre-degradation can be performed prior to laser-cutting. In such embodiments, pre-degradation of the extruded tubing, expanded tubing, or on the PLLA resin prior to extrusion if no commercial resin meets design requirements of molecular weight.

In some embodiments, the pre-degradation by the fluid can be performed at ambient temperature, i.e., any temperature between and including 20° C. to 30° C. In other embodiments, the pre-degradation may be performed at a temperature less than ambient or greater than ambient. The pre-degradation at a selected temperature is performed by exposing the scaffolding, tube, or resin to a fluid that is at the selected temperature. Since degradation occurs faster as temperature is increased, the pre-degradation time can be shortened if performed at temperatures higher than ambient. In some embodiments, the pre-degradation temperature can be 40-70° C. or 50° C. to 70° C. More narrowly, the pre-degradation temperature is 40-45° C., 40-70° C., 45-50° C., 50-55° C. 55-60° C., 60-65° C., or 65-70° C.

After the pre-degradation, the scaffold, tube, or resin is removed from the pre-degradation fluid and then rinsed in water to remove residual pre-degradation fluid or salts. The rinsed scaffold may then be dried under vacuum.

The pre-degraded scaffold, tube, or resin is pre-degraded to a target Mn that will provide a Mn(0) that provides desired degradation time and/or time of loss of radial strength. Thus, determining a pre-degraded resin target Mn must take into account the decrease in Mn throughout the entire manufacturing process, in particular, extrusion and sterilization. Determining a pre-degraded extruded or expanded tube target Mn must take into account the decrease in Mn throughout the remainder of the manufacturing process, in particular, sterilization. Determining a pre-degraded scaffolding target Mn must take into account the decrease in Mn throughout the remainder of the manufacturing process, in particular, sterilization. The pre-degradation time depends on the temperature of pre-degradation process since the degradation rate depends on the temperature.

Figure 11:
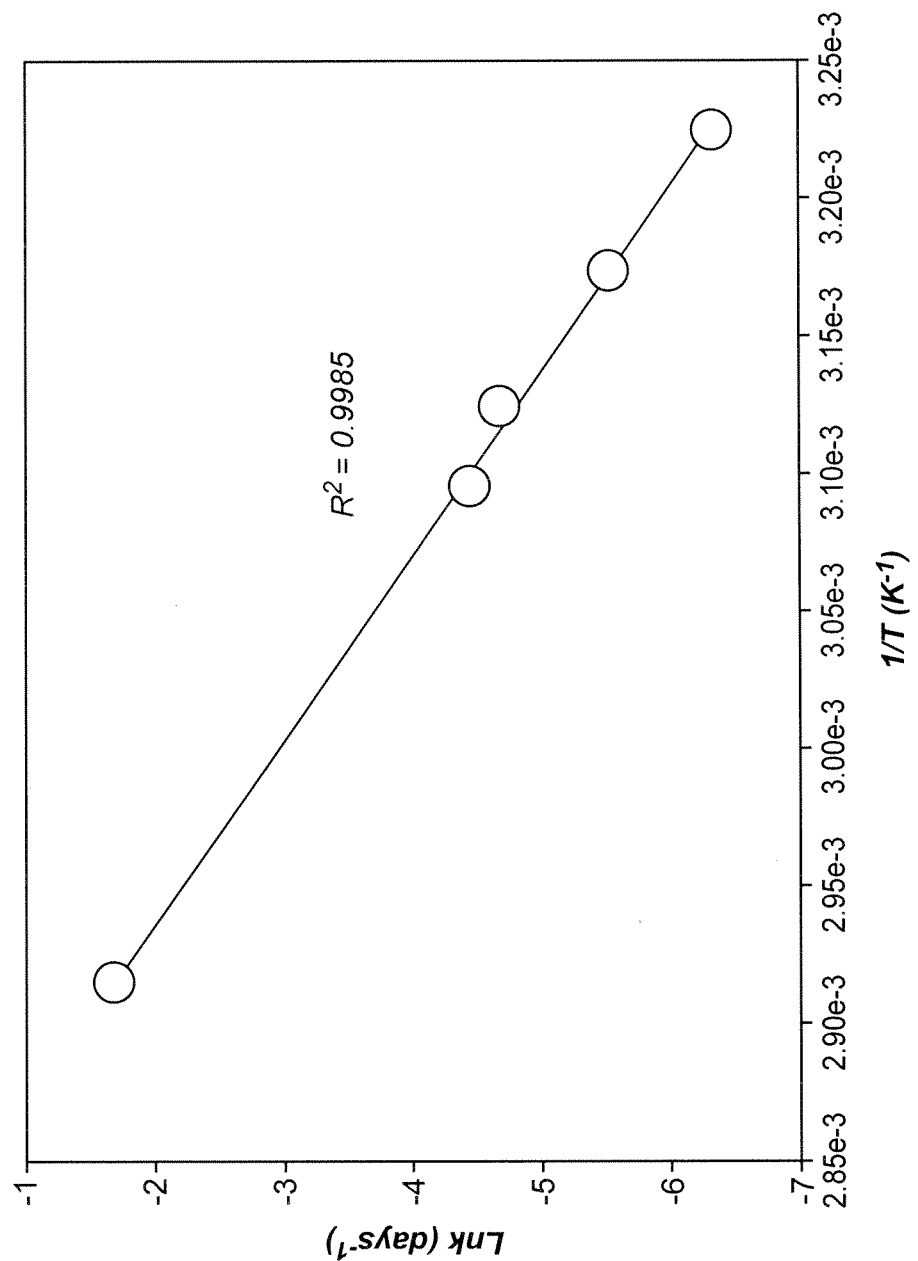
FIG. 11 shows the log k (rate content) vs. 1/T in the relevant temperature range for PLLA samples degrading in a PBS buffer.

The inventors have found from experiments that the degradation mechanism of the scaffolding remains unchanged within higher temperature ranges as compared to that of the degradation temperature in the human body, approximately 37° C. FIG. 11 shows the log k (rate content) vs. 1/T in the relevant temperature range for PLLA samples degrading in a PBS buffer. The excellent linear fit of the data shows that the degradation kinetic model applies at all temperatures tested. Therefore, once deployed in patients, the PLLA scaffolds products treated with pre-degradation are expected to degrade in the same manner as scaffolds that are not pre-degraded.

Figure 12:
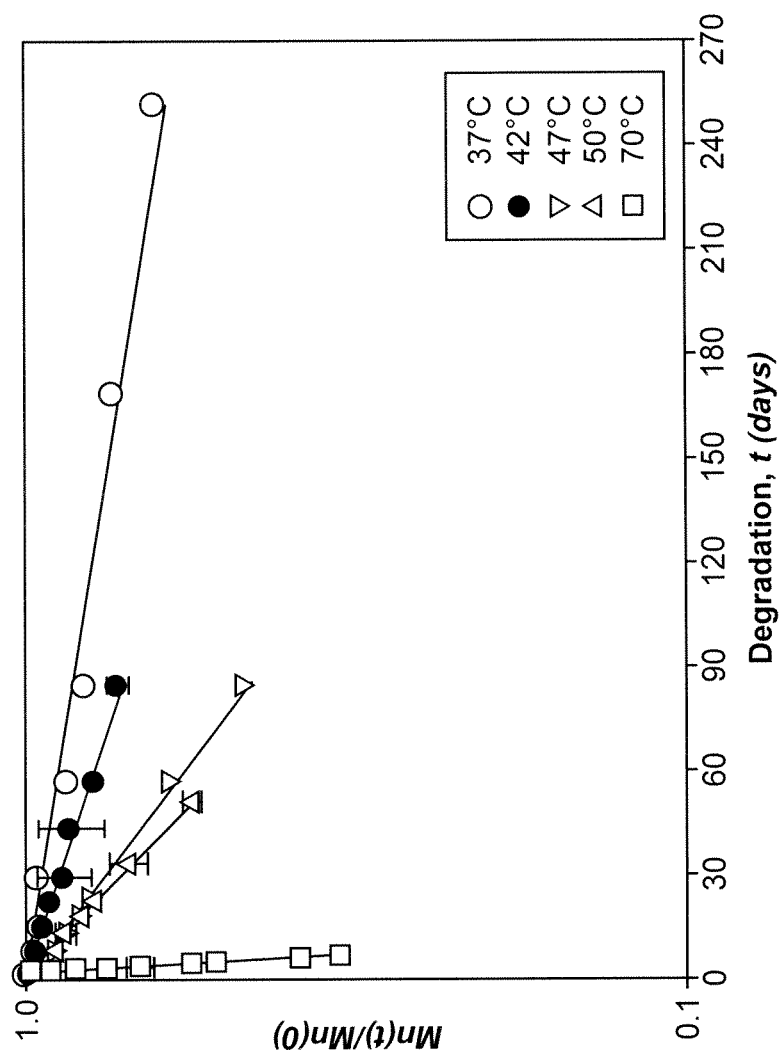
FIG. 12 depicts a normalized Mn vs. time of pre-degradation at five temperatures.

FIG. 12 depicts the Mn(t) vs. time of pre-degradation at five temperatures. The M(t) is normalized by the molecular weight prior to the pre-degradation. The required pre-degradation time to achieve the desired initial molecular weight can be estimated from FIG. 12. For example, to cut down molecular weight (Mn) of pre-sterilized scaffold from 250 kDa to 100 kDa, the lased scaffold would be pre-degraded in PBS buffer at 70° C. for approximately 5 days.

The embodiments described above include adjusting the molecular weight of the finished scaffold with radiation to obtain desired degradation properties. As discussed, a PLLA scaffolding made from resin of about 350 kDa, a 0.1 wt % monomer concentration that is processed as described results in an Mn(0) of about 100-110 kDa which has a 2.5 to 3 yr degradation time, which may be higher than desired for coronary treatment or other applications.

The scaffolding may further include a drug delivery coating over the scaffolding composed of a bioabsorbable polymer and drug, such as an antiproliferative agent. The bioabsorbable polymer acts as a carrier of the drug and controls the release of the drug. The purpose of this drug is to reduce smooth cell proliferation that occurs during a period up to 1-3 months after implantation of the scaffolding. The drug release profile (amount of drug release vs. time or cumulative drug release vs. time, time period of drug release) is governed, mediated, or controlled by the absorption of polymer carrier or coating.

As for any bioabsorbable polymer, the degradation profile of the polymer carrier depends on its initial molecular weight. The lower the starting molecular weight of the polymer carrier, the shorter is the release time of antiproliferative. In general, the release profile of any drug in the carrier will depend on the starting molecular weight of the carrier. In general, there is a minimum range of drug release time to treat the smooth cell proliferation which is about 1-3 months. Thus, the drug release profile of the coating should meet this limitation.

Any radiation exposure to the stent scaffolding after coating the scaffolding will not only reduce the molecular weight of the scaffolding, but also reduce the molecular weight of the polymer carrier of the coating. The reduction in carrier's molecular weight will impact the drug release profile. Specifically, the degradation time of the carrier will decrease which will shorten the time period of drug release. Therefore, the molecular weight (Mn) of the polymer carrier prior to any radiation exposure should be selected so that after any radiation exposure the Mn is high enough to provide a desired minimum drug release time.

In other embodiments, both the PLLA resin for the scaffolding and PDLLA resin for the coating may be selected to provide a desired degradation profile. In particular, these resins are selected so that the Mn(0) of the scaffolding and coating provide respective desired degradation profiles. In addition, these resins are also selected so that the monomer content of the scaffolding and coating provide respective desired degradation profiles.

Referring back to the previous example, a PLLA resin with a high Mn of about 350 kDa and monomer content up to 0.1% used for scaffold preparation results in a scaffold after a terminal sterilization with a Mn of 100-110 which has a degradation time of 2.5 to 3 years. A coating including a polymer carrier may be made from a PDLLA resin with a Mn of about 47 kDa and monomer content up to even 4%. The mass loss of the polymer carrier may start to happen within just several weeks after implantation.

It would be desirable to decrease the degradation time of the scaffolding and increase the degradation time of the coating. In some embodiments, the Mn and monomer content of both a PLLA resin for a scaffold and PDLLA resin for a coating are adjusted or selected to obtain desired degradation profiles for the scaffolding and the coating, such as degradation times.

As discussed above, a Mn(0) and MCs can be determined that correspond to the desired degradation profile. Thus, the Mn and monomer content of resin can be varied to obtain the Mn(0) and MCs that correspond to the desired degradation profile. The Mn(0) and MCs obtained correspond to specific processing conditions since Mn is affected by extrusion conditions and radiation dose and the monomer content is affected by extrusion conditions. In further embodiments, the extrusion conditions, primarily temperature, can also be adjusted to obtain the desired degradation profile.

For example, a desired degradation profile for the scaffolding includes a degradation time of 16-20 months. The desired degradation time of the PDLLA coating polymer is between 2-3 months. These degradation properties can be obtained with a PLLA scaffolding fabricated from resin with a Mn(0) of 150-200 kDa and PDLLA coating Mn(0) of 70-100 kDa.

Stent Structure/Property Data for In Vitro Studies

The stent scaffold pattern used in the in vitro studies discussed herein corresponds to the pattern described in U.S. application Ser. No. 12/447,758 (US 2010/0004735) to Yang & Jow, et al. Cross-section of the struts of the scaffold is 150×150 microns.

EXAMPLES

Example 1

Figure 13:
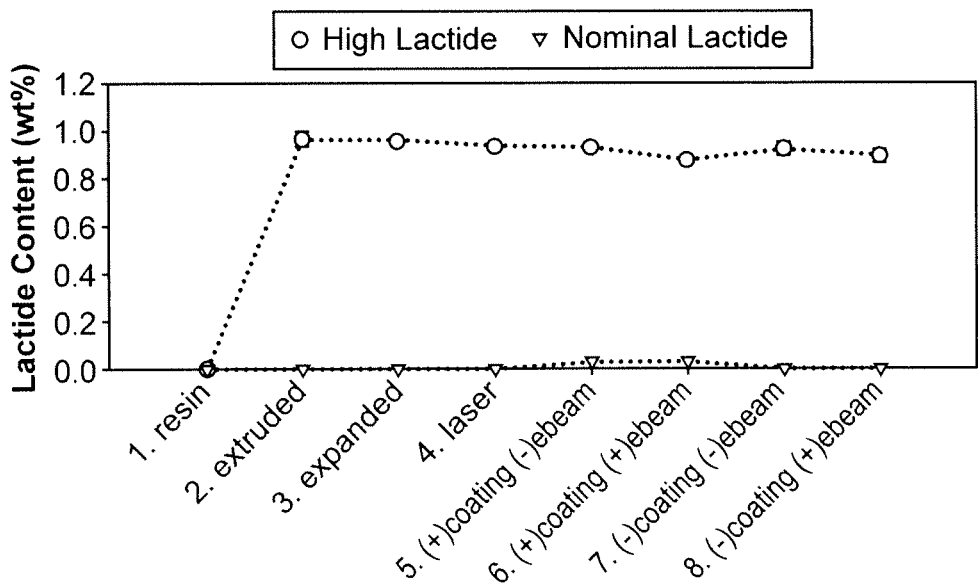
FIG. 13 shows the PLLA scaffolding manufacture process effect on monomer lactide generation.

Demonstration that Extrusion was the Most Significant Contributor to the Lactide Content FIG. 13 shows the PLLA scaffolding manufacture process effect on monomer lactide generation. Two extruded tubing lots were produced with a nominal (<0.02 wt %) and a high (0.97±0.03 wt %). At the nominal lactide concentration (<0.02 wt %), a slight increase in lactide content was detected from extruded tubing to the finished goods (FGs). This was due to the lactide content in the PDLLA coating polymer, which was not expected to contribute to the PLLA scaffold degradation, because once in contact with water, the lactide would elute out considering the thin PDLLA coating and the high solubility of lactide in water. Hence, lactide content in extruded tubes represented that in the FGs. For the extrusion tubing lot with high lactide content (0.97±0.03 wt %), a slight decrease was observed from extruded tubes to the FGs. This decrease was attributed to the increased probability of ester bond cleavage in the cyclic lactide monomer due to electron beam energy. This would result in other forms of low-molecular-weight species, such as di-lactic acid, leading to an equivalent effect on degradation. Such phenomenon is not observed at the lower level as the proposed lactide content limit. In this case, the extruded tubes represent the worst case scenario of lactide content compared to the corresponding FGs.

Example 2

Showing that Lactide Content in the Extruded Tubes was Equivalent to that in FGs Four groups of finished PLLA scaffoldings (FGs) were fabricated from extruded tubing lots with various levels of lactide content (0.02 (nominal), 0.17, 0.57, and 1.08 wt % lactide) by spiking (adding) a pre-determined amount of L-lactide into the PLLA resin prior to extrusion. For all FGs, groups, n=10. For extruded tubing groups, n=2 for groups "1.08 wt %" and "0.02 wt %"; n=10 for group "0.17 wt %"; n=21 for group "0.57 wt %". The error bars represent one standard deviation.

Figure 14:
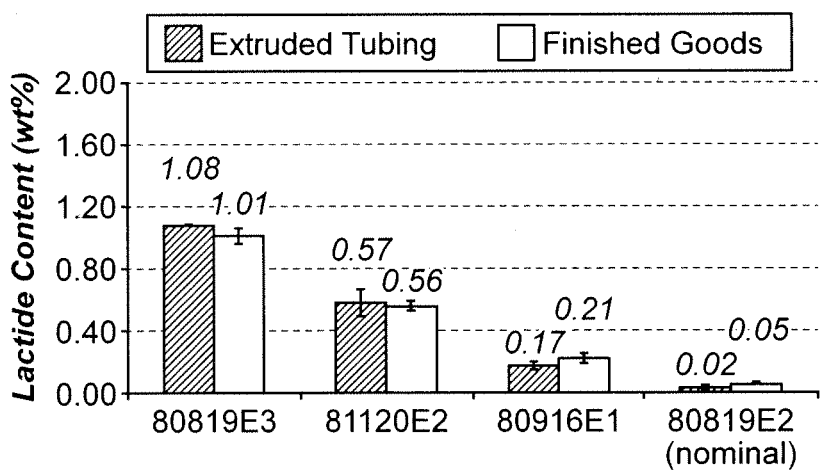
FIG. 14 shows the lactide content in the extruded tubes from Gas Chromatography—Flammable Ionization Detection.

FIG. 14 shows the lactide content in the extruded tubes from Gas Chromatography—Flammable Ionization Detection. FIG. 14 shows that the lactide content in extruded tubes was either equivalent to that in FGs or represented the worst case scenario in terms of the effect on degradation. Additionally, FIG. 14 shows that the loss of lactide content from extruded tubes to FGs diminished with the decrease in lactide content in the extruded tubes. When the extruded tubes contained approximately 0.5 wt % or less lactide, lactide content between extruded tubes and FGs either remained unchanged or increased slightly, which again was due to the known amount of lactide in the PDLLA coating polymer. Hence, at lactide content level of 0.5 wt %, controlling lactide content in extruded tubes is sufficient to control lactide content in FGs. This data shows by that the loss of lactide content at higher level was caused by the increased probability of the lactide molecules being cleaved; yielding other forms of low-molecular-weight species that were expected to exert the same effect on degradation. Therefore, the lactide content in the extruded tubes was determined to be equivalent to that in the corresponding FGs in terms of the effect on degradation.

Example 3

Figure 15:
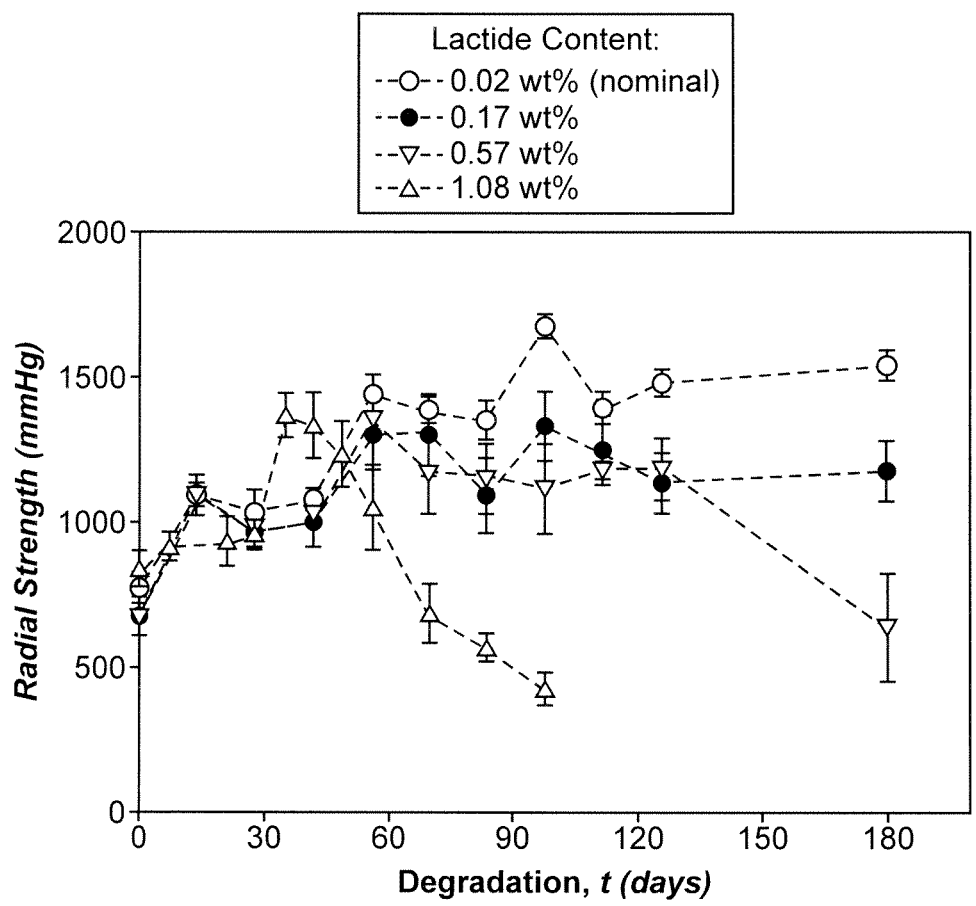
FIG. 15 depicts the radial strength progression over degradation as a function of lactide content of the four lots of extruded tubing from Example 2.

Lactide Blending in Extrusion: Effect on Radial Strength Change during In Vitro Degradation FIG. 15 depicts the radial strength progression over degradation as a function of lactide content of the four lots of extruded tubing from Example 2. Each data point represents n=6. Error bars represent one standard deviation. The radial strength progression over degradation time was tracked. FIG. 15 shows that the higher lactide content shortened the duration that radial strength was maintained in FGs. Although such an effect was not demonstrated for lactide content levels "0.02 wt %" and "0.17 wt %" in this study due to limited experimental time duration, it is expected that similar results would be observed in these lactide content levels.

Although such an effect was not demonstrated for lactide content levels "0.02 wt %" and "0.17 wt %" in this study due to limited experimental time duration, it is expected that similar results would be observed in these lactide content levels.

Example 4

Determination of Mn,Tr for PLLA Scaffolding

Table 1 summarizes two studies used to determine Mn,Tr for a PLLA scaffold. As shown in Table 1, each study concluded a range that $Mn,_{Tr}$ lies within.

TABLE 2

Summary of $Mn,_{Tr}$ and Mn,c

| Study | Mechanical Test Output | Test Samples | $Mn,_{Tr}{}^c$ On-set of Mechanical Strength Decrease |
|---|---|---|---|
| [a]1 | Radial Strength | FGs with 0.51 wt % lactide content | 24 kDa < $Mn,_{Tr}$ ≤ 47 kDa |
|  |  | FGs with 0.95 wt % lactide content | 45 kDa < $Mn,_{Tr}$ ≤ 52 kDa |
| [b]2 | Tensile Strength | Circumferential Dogbones | 40 kDa < $Mn,_{Tr}$ ≤ 51 kDa |

[a]No radial strength loss was observed for FGs with ca. 0.05 wt % or ca. 0.19 wt % lactide content up to the studied time period. Data on FGs with ca. 2.70 wt % lactide content is excluded from the analysis, since such high lactide content may induce defects to the PLLA backbone morphology, resulting in the data being unrepresentative.
[b]Axial dogbone data is excluded from analysis as the axial direction is determined to be less clinically relevant.
[c]Mn data was tested by gel permeation chromatography (GPC).

Radial strength testing on FGs with 0.95 wt % lactide content yielded an Mn,Tr that falls between 52 kDa and 45 kDa, which is in alignment with the upper limit of 51 kDa obtained from tensile testing on circumferential dogbones. In vitro degradation study on FGs with 0.51 wt % of lactide content further analyzed Mn,Tr more precisely by demonstrating that the degraded scaffold with an Mn of 47 kDa was still capable of maintaining high radial strength. Hence, 47 kDa is chosen as the Mn,Tr for a PLLA bioabsorbable scaffold.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a bioabsorbable stent comprising:
   providing a PLLA polymer scaffolding, wherein the PLLA polymer scaffolding has an Mn of at least 250 kDa;
   exposing the scaffolding to a first radiation dose prior to crimping to reduce the Mn;
   crimping the exposed scaffolding to a reduced diameter over a delivery balloon; and
   exposing the crimped scaffolding to a second radiation dose of 20-31 kGy for sterilization which reduces the Mn to an Mn(0), wherein the Mn(0) provides a degradation time of 16-20 months and a time of loss of radial strength of at least about 3 months.

2. The method of claim 1, wherein the monomer content of the sterilized scaffold is 0-0.1 wt %, 0.1-0.2 wt %, 0.2-0.5 wt %, or 0.5-1 wt %, and the Mn after the second radiation dose is 55-110 kDa.

3. The method of claim 1, wherein the first radiation dose is 6-50 kGy.

* * * * *